(12) United States Patent
Ayers et al.

(10) Patent No.: US 11,326,211 B2
(45) Date of Patent: May 10, 2022

(54) BLOOD-BASED BIOMARKERS OF TUMOR SENSITIVITY TO PD-1 ANTAGONISTS

(71) Applicant: Merck Sharp & Dohme Corp., Rahway, NJ (US)

(72) Inventors: Mark Ayers, Pennington, NJ (US); Jared Lunceford, Washington, UT (US); Andrey Loboda, Boston, MA (US); Michael Nebozhyn, Colmar, PA (US); Terrill K. McClanahan, Sunnyvale, CA (US); Heather Hirsch, Brookline, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 648 days.

(21) Appl. No.: 15/565,233

(22) PCT Filed: Apr. 12, 2016

(86) PCT No.: PCT/US2016/027014
§ 371 (c)(1),
(2) Date: Oct. 9, 2017

(87) PCT Pub. No.: WO2016/168133
PCT Pub. Date: Oct. 20, 2016

(65) Prior Publication Data
US 2018/0148790 A1 May 31, 2018

Related U.S. Application Data

(60) Provisional application No. 62/149,333, filed on Apr. 17, 2015.

(51) Int. Cl.
| | | |
|---|---|---|
| *C12Q 1/6886* | (2018.01) | |
| *A61K 39/395* | (2006.01) | |
| *G01N 33/543* | (2006.01) | |
| *G01N 33/566* | (2006.01) | |
| *G01N 33/574* | (2006.01) | |
| *G01N 33/68* | (2006.01) | |

(52) U.S. Cl.
CPC ...... *C12Q 1/6886* (2013.01); *A61K 39/39558* (2013.01); *G01N 33/543* (2013.01); *G01N 33/566* (2013.01); *G01N 33/574* (2013.01); *G01N 33/68* (2013.01); *C12Q 2600/106* (2013.01); *C12Q 2600/158* (2013.01); *G01N 2800/52* (2013.01)

(58) Field of Classification Search
CPC .. G01N 33/543; G01N 33/566; G01N 33/574; G01N 3/68; G01N 2800/52; C12Q 1/6886; C12Q 2600/106; C12Q 2600/158
See application file for complete search history.

(56) References Cited

U.S. PATENT DOCUMENTS

| | | | |
|---|---|---|---|
| 7,521,051 B2 | 4/2009 | Collins et al. | |
| 8,008,449 B2 | 8/2011 | Korman et al. | |
| 8,354,509 B2 | 1/2013 | Carven et al. | |
| 8,383,796 B2 | 2/2013 | Korman et al. | |
| 9,535,074 B2 | 1/2017 | Ayanoglu et al. | |
| 2013/0034540 A1 | 2/2013 | Mule et al. | |
| 2013/0178391 A1* | 7/2013 | Bergstrom | ........... C12Q 1/6886 506/9 |
| 2013/0330325 A1* | 12/2013 | Grabe | ................. G01N 33/6893 424/133.1 |
| 2014/0220580 A1 | 8/2014 | Brown et al. | |
| 2015/0071910 A1* | 3/2015 | Kowanetz | .......... C07K 16/2827 424/133.1 |
| 2018/0327848 A1 | 11/2018 | Ayers | |

FOREIGN PATENT DOCUMENTS

| | | |
|---|---|---|
| CA | 2905798 A1 | 9/2014 |
| EP | 2535354 A1 | 12/2012 |
| WO | 2008156712 | 12/2008 |
| WO | 2010027827 | 3/2010 |
| WO | 2010077634 | 7/2010 |
| WO | 2011066342 | 6/2011 |
| WO | 2012038068 A1 | 3/2012 |
| WO | 2012135408 | 10/2012 |
| WO | 2013019906 | 2/2013 |
| WO | 2014009535 A2 | 1/2014 |
| WO | 2014165422 A1 | 10/2014 |

(Continued)

OTHER PUBLICATIONS

Callahan M., At the Bedside: CTLA-4-and PD-1-blocking antibodies in cancer immunotherapy, Jul. 2013, Journal of Leukocyte Biology, 94, p. 41-53 (Year: 2013).*
NIH, ClinicalTrials.gov Identifier: NCT01295827, 2019, NIH, p. 1 (Year: 2019).*
Muenst et al., The PD-1/PD-L1 pathway: biologicval background and clinical relevance of an emerging treatment target in immunotherapy, Dec. 10, 2014, Expert Opinion on Therapeutic Targets, 19(2), p. 201-211 (Year: 2014).*
Lal et al., An immunogenomic stratification of colorectal cancer: Implications for development of targeted immunotherapy, Mar. 2015 ., Oncolmmunology, 4(3), p. 1-9 and supplemental (Year: 2015).*

(Continued)

*Primary Examiner* — Olivia M. Wise
*Assistant Examiner* — Kaitlyn L Minchella
(74) *Attorney, Agent, or Firm* — Sarah L. Hooson; Alysia A. Finnegan

(57) ABSTRACT

The present disclosure describes baseline and on treatment blood-based gene signature biomarkers that are predictive of tumor sensitivity to therapy with a PD-1 antagonist. The on-treatment biomarkers comprise a PD-L1 gene signature or an interferon gamma gene signature and the baseline gene signature biomarker comprises genes associated with the oxidative phosphorylation pathway. The disclosure also provides methods and kits for testing tumor samples for these biomarkers, as well as methods for treating subjects with a PD-1 antagonist based on the test results.

18 Claims, 14 Drawing Sheets

(56) References Cited

FOREIGN PATENT DOCUMENTS

| WO | 2014194293 | A1 | 12/2014 |
|---|---|---|---|
| WO | 2015016718 | | 2/2015 |
| WO | 2015035112 | A1 | 3/2015 |
| WO | 2015094992 | | 6/2015 |
| WO | 2015094992 | A1 | 6/2015 |
| WO | 2015094995 | | 6/2015 |
| WO | 2015094996 | | 6/2015 |
| WO | 2015119930 | A1 | 8/2015 |
| WO | 2016094094377 | | 6/2016 |

OTHER PUBLICATIONS

Postow et al., Immune Checkpoint Blockade in Cancer Therapy, 2015, Journal of Clinical Oncology, 33(17), p. 1974-1982 (Year: 2015).*
Burczynski et al., Transcriptional profiling of peripheral blood cells in clinical pharmacogenomic studies, 2006, Pharmacogenomics, 7(2), p. 187-202 (Year: 2006).*
Brahmer et al., Safety and Activity of Anti-PD-L1 Antibody in Patients with Advanced Cancer, 2012, N Engl J Med, 366(26), p. 2455-2465 (Year: 2012).*
Chow et al., Biomarkers and response to pembrolizumab (pembro) in recurrent/metastatic head and neck squamous cell carcinoma (R/M HNSCC), Journal of Clinical Oncology, 2016, Abstract 6010, vol. 34, No. 15.
Ahmadzadeh et al., Tumor antigen-specific CD8 T cells infiltrating the tumor express high levels of PD-1 and are functionally impaired, Blood, 2009, 1537-1544, 114.
Dong et al., Tumor-associated B7-H1 promotes T-cell apoptosis: A potential mechanism of immune evasion, Nature Medicine, 2002, 793-800, 8(8).
Gao et al., Overexpression of PD-L1 Significantly Associates with Tumor Aggressiveness and Postoperative Recurrence in Human Hepatocellular Carcinoma, Clinical Cancer Research, 2009, 971-979, 15.
Geiss et al., Direct multiplexed measurement of gene expression with color-coded probe pairs, Nature Biotechnology, 2008, 317-325, 26(3).
Ghebeh et al., FOXP3+ Tregs and B7-H1+/PD-1+T lymphocytes co-infiltrate the tumor tissues of high-risk breast cancer patients: Implication for immunotherapy, BMC Cancer, 2008, 57-68, 8.
Ghebeh et al., The B7-H1 (PD-L1) T Lymphocyte-inhibitory Molecule Is Expressed in Breast Cancer Patients with Infiltrating Ductal Carcinoma: Correlation with Important High-Risk Prognostic Factors, Neoplasia, 2006, 190-198, 8.
Hamanishi et al., Programmed cell death 1 ligand 1 and tumor-infiltrating CD8+ T lymphocytes are prognostic factors of human ovarian cancer, Proceedings of the National Academy of Sciences USA, 2007, 3360-3365, 104.
Hino et al., Tumor cell expression of programmed cell death-1 ligand 1 is a prognostic factor for malignant melanoma, Cancer, 2010, 1757-1766, 116(7).
Inman et al., PD-L1 (B7-H1) expression by urothelial carcinoma of the bladder and BCG-induced granulomata: associations with localized stage progression, Cancer, 2007, 1499-1505, 109.
J. Compton, Nucleic acid-sequence based amplification, Nature, 1991, pp. 91-92, 350(6313).
Martel et al., Multiplexed Screening Assay for mRNA Combining Nuclease Protection with Luminescent Array Detection, Assay and Drug Development Technologies, 2002, 61-71, 1(1).
N. Lal, An immunogenomic stratification of colorectal cancer: Implications for development of targeted immunotherapy, OncoImmunology, Apr. 2, 2015, pp. 1-9, vol. 4, No. 3.
Nakanishi et al., Overexpression of B7-H1 (PD-L1) significantly associates with tumor grade and postoperative prognosis in human urothelial cancers, Cancer Immunol. Immunother., 2007, 1173-1182, 56.
Nomi et al., Clinical Significance and Therapeutic Potential of the Programmed Death-1 Ligand/Programmed Death-1 Pathway in Human Pancreatic Cancer, Clinical Cancer Research, 2007, 2151-2157, 13.
Ohigashi et al., Clinical Significance of Programmed Death-1 Ligand-1 and Programmed Death-1 Ligand-2 Expression in Human Esophageal Cancer, Clin. Cancer Research, 2005, 2947-2953, 11.
Sharpe et al., The function of programmed cell death 1 and its ligands in regulating autoimmunity and infection, Nature Immunology, 2007, 239-245, 8.
Shimauchi et al., Augmented expression of programmed death-1 in both neoplastic and non-neoplastic CD4+ T-cells in adult T-cell leukemia/lymphoma, Int. J. Cancer, 2007, 2585-2590, 121.
Simon et al., Regularization Paths for Cox's Proportional Hazards Model via Coordinate Descent, Journal of Statistical Software, 2011, pp. 1-16, vol. 39(5).
Thompson et al., PD-1 is Expressed by Tumor-Infiltrating Immune Cells and Is Associated with Poor Outcome for Patients with Renal Cell Carcinoma, Clinical Cancer Research, 2007, 1757-1761, 15.
Thompson et al., Significance of B7-H1 Overexpression in Kidney Cancer, Cancer, 2006, 206-211, 5.
WHO Drug information, vol. 27, No. 1, pp. 68-69 (2013).
WHO Drug information, vol. 27, No. 2, pp. 161-162 (2013).
Yang et al., PD-L1: PD-1 interaction Contributes to the Functional Suppression of T-Cell Responses to Human Uveal Melanoma Cells In Vitro, Invest Ophthalmol Vis Sci, 2008, 2518-2525, 49(6).
Zou et al., Regularization and variable selection via the elastic net, J. R. Statist. Soc. B, 2005, 301-320, 67(2).
Yervoy 5 mg/ml concentrate solution for infusion' —summary of product characteristics. Electronic Medicines Compendium, Available online (https://www.medicines.org.Uk/emc/medicine/24779#gref), retrieved Sep. 12, 2021 (supplementary material / evidence, not citeable as prior art under Art. 54 EPC), 28 pages.
Brooks, James D., Translational genomics: The challenge of developing cancer biomarker, Genome Research, 2012, 183-187, 22(2).
Goossens, Nicolas et al., Cancer biomarker discovery and validation, Transl. Cancer Res., 2015, 256-269, 4(3).
Keytruda CDER Summary Review (published Sep. 4, 2014), 24 pages.
Keytruda Prescribing Information (revised Sep. 2014), 16 pages.
Lal, Neeraj et al., An immunogenomic stratificiton of colorectal cancer: Implications for development of targeted Immunotherapy (Supplementary Information), OncoImmunology, 2015, Tables S1-S3, vol. 4, No. 3.
Notice of Opposition dated Sep. 28, 2021 in corresponding EP Application No. 16780526.6.

\* cited by examiner

BLOOD-BASED BIOMARKERS OF TUMOR SENSITIVITY TO PD-1 ANTAGONISTS

CROSS-REFERENCE TO RELATED APPLICATIONS

This application is a § 371 National Phase Application of International Application No. PCT/US2016/027019, filed Apr. 12, 2016, which claims the benefit of U.S. Application No. 62/149,333, filed Apr. 17, 2015.

FIELD OF THE INVENTION

The present invention relates generally to the treatment of cancer. In particular, the invention relates to methods for identifying patients who are likely to experience an anti-tumor response to treatment with an antagonist of Programmed Death 1 (PD-1).

BACKGROUND OF THE INVENTION

PD-1 is recognized as an important molecule in immune regulation and the maintenance of peripheral tolerance. PD-1 is moderately expressed on naive T, B and NKT cells and up-regulated by TB cell receptor signaling on lymphocytes, monocytes and myeloid cells (1).

Two known ligands for PD-1, PD-L1 (B7-H1) and PD-L2 (B7-DC), are expressed in human cancers arising in various tissues. In large sample sets of e.g. ovarian, renal, colorectal, pancreatic, liver cancers and melanoma, it was shown that PD-L1 expression correlated with poor prognosis and reduced overall survival irrespective of subsequent treatment (2-13). Similarly, PD-1 expression on tumor infiltrating lymphocytes was found to mark dysfunctional T cells in breast cancer and melanoma (14-15) and to correlate with poor prognosis in renal cancer (16). Thus, it has been proposed that PD-L1 expressing tumor cells interact with PD-1 expressing T cells to attenuate T cell activation and evasion of immune surveillance, thereby contributing to an impaired immune response against the tumor.

Several monoclonal antibodies that inhibit the interaction between PD-1 and one or both of its ligands PD-L1 and PD-L2 are in clinical development for treating cancer. These include nivolumab and pembrolizumab, which are antibodies that bind to PD-1, and MPDL3280A, which binds to PD-L1. While clinical studies with these antibodies have produced durable anti-tumor responses in some cancer types, a significant number of patients failed to exhibit an anti-tumor response. Thus, a need exists for diagnostic tools to identify which cancer patients are most likely to achieve a clinical benefit to treatment with a PD-1 antagonist.

An active area in cancer research is the identification of gene expression patterns, commonly referred to as gene signatures or molecular signatures, which are characteristic of particular types or subtypes of cancer, and which may be associated with clinical outcomes. For example, co-pending international patent applications PCT/US14/070236, PCT/US14/070232, and PCT/US14/070237, each of which was filed on 15 Dec. 2014, describe various gene signatures for tumor tissue that are predictive biomarkers of patients producing an anti-tumor response following subsequent treatment with the PD-1 antagonist pembrolizumab. However, to avoid the requirement for tumor tissue to test a patient for a predictive biomarker, it would be desirable to identify blood-based biomarkers that can be utilized before or during treatment with a PD-1 antagonist to identify patients who are most likely to benefit from, or be resistant to, such immunotherapy.

SUMMARY OF THE INVENTION

The present invention provides baseline and on treatment blood-based gene signatures that are predictive biomarkers of tumor sensitivity to therapy with a PD-1 antagonist. Each of these blood-based biomarkers comprises a gene signature, i.e., a specific set of genes, and a gene signature score, which is an arithmetic composite of the normalized RNA expression levels of all of the genes in the signature that have been measured in intracellular RNA isolated from a blood sample.

In some embodiments, the gene signature biomarker is an on treatment biomarker, and the patient is positive for the biomarker if the gene signature score for a blood sample obtained after the patient has received at least one dose of the PD-1 antagonist is greater than the gene signature score for a baseline blood sample from the patient, e.g., prior to treatment with the PD-1 antagonist.

In an embodiment, the gene signature in an on treatment biomarker comprises PD-L1 and at least four other genes that are co-expressed with PD-L1, i.e., a PD-L1 gene signature. In an embodiment, the set of genes in a PD-L1 gene signature on-treatment biomarker comprises a five-gene or six-gene signature shown in Tables 1A and 1B below, respectively. In some embodiments, the expression level of each gene in a PD-L1 gene signature is assessed by measuring the level of each target transcript listed in Table 1A or Table 1B.

TABLE 1

Exemplary PD-L1 Gene Signatures

| Table 1A | | Table 1B | |
|---|---|---|---|
| Five Gene Signature | Target Transcript | Six Gene Signature | Target Transcript |
| PD-L1 | NM_014143 | PD-L1 | NM_014143 |
| PD-L2 | NM_025239 | PD-L2 | NM_025239 |
| LAG3 | NM_002286 | LAG3 | NM_002286 |
| STAT1 | NM_007315 | STAT1 | NM_007315 |
| CXCL10 | NM_001565 | CXCL10 | NM_001565 |
| | | CLEC10a | NM_182906 |

In another embodiment, the gene signature in an on-treatment biomarker comprises a specific set of at least about 5 to about 10 of the genes listed in Table 2 below. Each of the genes in Table 2 has a biological relationship to interferon-gamma (IFNG) signaling and thus is referred to herein as an IFNG-related gene. In some embodiments, the expression level of each gene in an IFNG gene signature is assessed by measuring the level of the corresponding target transcript listed in Table 2A. Exemplary IFNG gene signatures that may comprise blood-based biomarkers of the invention are shown in Tables 2B, 2C and 2D below.

TABLE 2

IFNG-related Genes and Exemplary IFNG gene signatures

| IFNG-Related Gene | Target Transcript (Table 2A) | Ten Gene Signature (Table 2B) | Six Gene Signature (Table 2C) | Five Gene Signature (Table 2D) |
|---|---|---|---|---|
| CCL4 | NM_002984.2 | | | |
| CCL5 | NM_002985.2 | | | |
| CCR5 | NM_000579.1 | CCR5 | | |
| CD2 | NM_001767.2 | | | |
| CD86 | NM_175862.3 | | | |
| CIITA | NM_000246.3 | | | |
| CXCL9 | NM_002416.1 | CXCL9 | CXCL9 | CXCL9 |
| CXCL10 | NM_001565.1 | CXCL10 | CXCL10 | CXCL10 |
| CXCL11 | NM_005409.3 | CXCL11 | | |
| GZMA | NM_006144 | GZMA | | |
| HLA-DRA | NM_019111.3 | HLA-DRA | HLA-DRA | HLA-DRA |
| IDO1 | NM_002164.3 | IDO1 | IDO1 | IDO1 |
| IFNG | NM_000619.2 | IFNG | IFNG | |
| KLRK1 | NM_007360.1 | | | |
| PRF1 | NM_001083116 | PRF1 | | |
| STAT1 | NM_007315.2 | STAT1 | STAT1 | STAT1 |

In another embodiment, the gene signature in an on-treatment biomarker comprises a combination of a PD-L1 signature listed in Table 1 and an IFNG signature listed in Table 2. In one embodiment, this PD-L1/IFNG combination signature consists of CCR5, CLEC10a, CXCL9, CXCL10, CXCL11, GZMA, HLA-DRA, IDO1, IFNG, LAG3, PD-L1, PD-L2, PRF1, and STAT1.

In some embodiments, the blood-based gene signature in a baseline biomarker comprises one or more of the oxidative phosphorylation (OxPhos) pathway genes listed in Table 3 below, and in an embodiment comprises 2 to 6, 3 to 7, 4 to 8, 5 to 10 or 6 to 11 of the Table 3 genes.

TABLE 3

Exemplary Genes for OxPhos Gene Signatures

| Symbol | Entrez Gene Name |
|---|---|
| ATP5G2 | ATP synthase, H+ transporting, mitochondrial Fo complex, subunit C2 |
| ATP5G3 | ATP synthase, H+ transporting, mitochondrial Fo complex, subunit C3 |
| ATP5J2 | ATP synthase, H+ transporting, mitochondrial Fo complex, subunit F2 |
| COX7C | cytochrome c oxidase subunit VIIc |
| NDUFA12 | NADH dehydrogenase (ubiquinone) 1 alpha subcomplex, 12 |
| NDUFA13 | NADH dehydrogenase (ubiquinone) 1 alpha subcomplex, 13 |
| NDUFA3 | NADH dehydrogenase (ubiquinone) 1 alpha subcomplex, 3, 9 kDa |
| NDUFA7 | NADH dehydrogenase (ubiquinone) 1 alpha subcomplex, 7, 14.5 kDa |
| NDUFB11 | NADH dehydrogenase (ubiquinone) 1 beta subcomplex, 11, 17.3 kDa |
| NDUFB4 | NADH dehydrogenase (ubiquinone) 1 beta subcomplex, 4, 15 kDa |
| NDUFS5 | NADH dehydrogenase (ubiquinone) Fe—S protein 5, 15 kDa |

To assess whether a patient's tumor is likely to respond to a PD-1 antagonist, the calculated score for a baseline blood sample obtained from the patient is compared to a reference score for the OxPhos gene signature that has been pre-selected to divide at least the majority of responders to therapy with the PD-1 antagonist from at least the majority of non-responders to anti-PD-1 therapy. If the patient has a baseline OxPhos gene signature score that is equal to or greater than the reference OxPhos gene signature score, the patient is less likely to respond to the PD-1 antagonist than if the patient's score is less than the reference score. In some embodiments, a patient with a baseline OxPhos gene signature score that is less than the reference score is classified as positive for an OxPhos gene signature biomarker and a patient with a baseline OxPhos signature score that is greater than the reference score is classified as negative for an OxPhos gene signature biomarker.

The inventors contemplate that determining signature scores for the blood based gene signatures described herein will be useful in a variety of research and clinical applications.

Thus, in one aspect, the invention provides a method for testing a patient with a tumor for the presence or absence of an on-treatment biomarker that is predictive of anti-tumor response to treatment with a PD-1 antagonist. The method comprises (a) obtaining a baseline blood sample from the patient, (b) isolating total intracellular RNA from the baseline sample, (c) measuring the baseline RNA expression level in the isolated RNA for each gene in a gene signature, (d) calculating a baseline signature score for the gene signature from the measured RNA expression levels, (e) obtaining a post-dose blood sample from the patient, (f) isolating total intracellular RNA from the post-dose sample, (g) measuring the post-dose RNA expression level in the isolated RNA for each gene in the gene signature, (h) calculating a post-dose signature score for the gene signature from the measured RNA expression levels, and (i) comparing the post-dose score to the baseline score, wherein the on-treatment biomarker is present if the post-dose signature score is greater than the baseline signature score and the on-treatment biomarker is absent if the post-dose signature score is equal to or less than the baseline signature score, wherein the gene signature is a PD-L1 gene signature or an IFNG gene signature described herein. Steps (b)-(d) of the method may be performed prior to, concurrently with, or after steps (f)-(h). In some embodiments, the steps (b)-(d) and steps (f)-(h) are performed concurrently. In some embodiments, the gene signature is any of the gene signatures listed in Tables 1 and 2. In an embodiment, the post-dose blood sample is obtained after a single dose of the PD-1 antagonist. In an embodiment, the PD-1 antagonist is administered to the patient on day 1 of a 2 or 3 week cycle, and the post-dose blood sample is obtained on the last day of the first cycle or on the first day of the second cycle, prior to administration of the second dose. In another embodiment, the post-dose blood sample is obtained after a second or subsequent dose of the PD-1 antagonist.

In another aspect, the invention provides a method for treating a patient having a tumor which comprises having a baseline blood sample from the patient analyzed to generate a baseline gene signature score for a PD-L1 gene signature or an IFNG gene signature, administering at least one dose of the PD-1 antagonist to the patient, having a post-dose blood sample from the patient analyzed to generate a post-dose gene signature score, and prescribing a treatment regimen based on the relative values of the baseline and post-dose gene signature scores, wherein if the post-dose score is greater than the pre-dose score, then the regimen is continued treatment with the PD-1 antagonist and if the post-dose score is equal to or less than the pre-dose score, then the regimen is treatment with a cancer therapy that does not include a PD-1 antagonist.

In another aspect, the invention provides a method for testing a patient with a tumor for the presence or absence of a baseline biomarker that is negatively correlated with response to treatment with a PD-1 antagonist. The method comprises obtaining a baseline blood sample from the patient, isolating total intracellular RNA from the baseline sample, measuring the RNA expression level in the isolated RNA for each gene in an OxPhos gene signature, and calculating a score for the OxPhos gene signature from the measured RNA expression levels. In some embodiments, the method further comprises comparing the calculated score to a reference score for the OxPhos gene signature, and classifying the patient as biomarker positive or biomarker negative. If the calculated score is equal to or greater than the reference score, then the patient is classified as biomarker negative, i.e., not likely to respond, and if the calculated OxPhos gene signature score is less than the reference OxPhos gene signature score, then the patient is classified as biomarker positive.

In a still further aspect, the invention provides a pharmaceutical composition comprising a PD-1 antagonist for use in treating a cancer in patients who (a) test positive for an on-treatment PD-L1 or IFNG gene signature biomarker or (b) test positive for a baseline OxPhos gene signature biomarker.

Yet another aspect of the invention is a drug product which comprises a pharmaceutical composition and prescribing information. The pharmaceutical composition comprises a PD-1 antagonist and at least one pharmaceutically acceptable excipient. The prescribing information states that the pharmaceutical composition is indicated for use in treating a cancer in patients who (a) test positive for on-treatment PD-L1 or IFN-γ gene signature biomarker or (b) test positive for a baseline OxPhos gene signature biomarker.

In another aspect, the invention provides a kit useful for assaying a blood sample to determine a score for a PD-L1, IFN-γ gene or OxPhos gene signature in the sample. The kit comprises a first set of probes for detecting expression of each gene in the gene signature. In some embodiments, the gene signature is any of the gene signatures listed in Table 1 and Table 2, and the kit comprises, for each target transcript in the gene signature, at least one probe for the target transcript. In some embodiments, the kit may also comprise a second set of probes for detecting expression of a set of normalization genes. The normalization gene set consists of any number of genes between 10 and 1000, e.g., this gene set may consist of at least any of 10, 20, 40, 80, 160, 320, and 640 genes. In an embodiment, the kit comprises a set of probes for detecting expression of each of the 680 genes listed in Table 4 below. The kit may also comprise a plurality of control blood samples which may be assayed for expression of the gene signature of interest and normalization genes in the same manner as the test blood sample.

In some embodiments of any of the above aspects of the invention, determining the score for a gene signature of interest in a blood sample comprises performing quantile normalization of raw RNA expression values for the genes in the gene signature relative to the distribution of raw RNA expression values for a set of at least 200, 250, 300, 350, 400 or 600 normalization genes, followed by a subsequent log 10-transformation. In an embodiment, the set of normalization genes comprises the signature genes and other genes. In an embodiment, the normalization gene set consists of all 680 genes in Table 4 below.

In all of the above aspects and embodiments of the invention, the PD-1 antagonist inhibits the binding of PD-L1 to PD-1, and preferably also inhibits the binding of PD-L2 to PD-1. In some embodiments, the PD-1 antagonist is a monoclonal antibody, or an antigen binding fragment thereof, which specifically binds to PD-1 or to PD-L1 and blocks the binding of PD-L1 to PD-1. In an embodiment, the PD-1 antagonist is pembrolizumab or nivolumab.

In some embodiments of any of the above aspects of the invention, the patient has bladder cancer, breast cancer, clear cell kidney cancer, head/neck squamous cell carcinoma, lung squamous cell carcinoma, malignant melanoma, non-small-cell lung cancer (NSCLC), ovarian cancer, pancreatic cancer, prostate cancer, renal cell cancer, small-cell lung cancer (SCLC) or triple negative breast cancer. In an embodiment, the patient has ipilimumab-naïve advanced melanoma, while in another embodiment the patient has ipilimumab-refractory advanced melanoma.

DETAILED DESCRIPTION

Abbreviations

Figure 1:
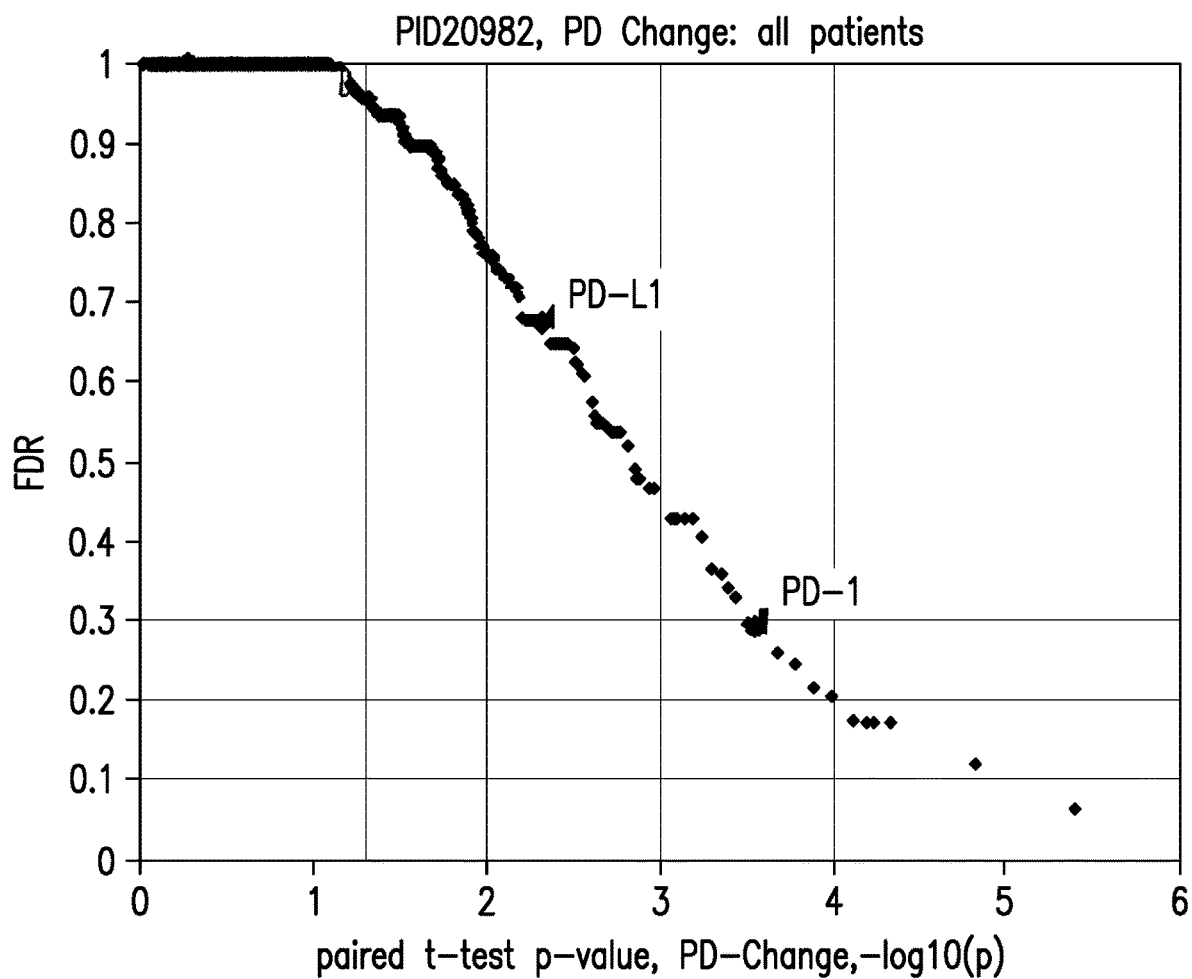
FIG. 1 is a scatter plot showing that statistically significant greater levels of PD-1 mRNA and PD-L1 mRNA were detected in blood samples obtained from a cohort of 44 melanoma patients who had been treated with a single dose of pembrolizumab (the MEL Cohort) compared to the PD-1 and PD-L1 levels detected in baseline blood samples from the cohort.

Throughout the detailed description and examples of the invention the following abbreviations will be used:
BOR Best objective response
CDR Complementarity determining region
CHO Chinese hamster ovary
CR Complete Response
DFS Disease free survival
FR Framework region
IFNG or IFN-γ Interferon gamma
irRC Immune related response criteria
NCBI National Center for Biotechnology Information
OR Objective response
OS Overall survival
PD Progressive Disease
PD-1 Programmed Death 1
PD-L1 Programmed Cell Death 1 Ligand 1
PD-L2 Programmed Cell Death 1 Ligand 2
PFS Progression free survival (PFS)
PR Partial Response
Q2W One dose every two weeks
Q3W One dose every three weeks
RECIST Response Evaluation Criteria in Solid Tumors
SD Stable Disease
VH Immunoglobulin heavy chain variable region
VK Immunoglobulin kappa light chain variable region I. Definitions So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"About" when used to modify a numerically defined parameter (e.g., the gene signature score for a gene signature discussed herein, or the dosage of a PD-1 antagonist, or the length of treatment time with a PD-1 antagonist) means that the parameter may vary by as much as 10% above or below the stated numerical value for that parameter. For example, a gene signature consisting of about 10 genes may have between 9 and 11 genes. Similarly, a reference gene signature score of about 2.462 includes scores of and any score between 2.2158 and 2.708.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human. The term "patient" refers to a human.

As used herein, the term "antibody" refers to any form of antibody that exhibits the desired biological or binding activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; $5^{th}$ ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). As used herein, the term "framework" or "FR" residues refers to those variable domain residues other than the hypervariable region residues defined herein as CDR residues.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies, or binding fragments thereof, useful in the present invention will bind to the target protein with an affinity that is at least two fold greater, preferably at least ten times greater, more preferably at least 20-times greater, and most preferably at least 100-times greater than the affinity with non-target proteins. As used herein, an antibody is said to bind specifically to a polypeptide comprising a given amino acid sequence, e.g. the amino acid sequence of a mature human PD-1 or human PD-L1 molecule, if it binds to polypeptides comprising that sequence but does not bind to proteins lacking that sequence.

"Chimeric antibody" refers to an antibody in which a portion of the heavy and/or light chain is identical with or homologous to corresponding sequences in an antibody derived from a particular species (e.g., human) or belonging to a particular antibody class or subclass, while the remainder of the chain(s) is identical with or homologous to corresponding sequences in an antibody derived from another species (e.g., mouse) or belonging to another antibody class or subclass, as well as fragments of such antibodies, so long as they exhibit the desired biological activity.

"Human antibody" refers to an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

"Anti-tumor response" when referring to a cancer patient treated with a therapeutic agent, such as a PD-1 antagonist, means at least one positive therapeutic effect, such as for example, reduced number of cancer cells, reduced tumor size, reduced rate of cancer cell infiltration into peripheral organs, reduced rate of tumor metastasis or tumor growth, or progression free survival. Positive therapeutic effects in cancer can be measured in a number of ways (See, W. A. Weber, J. Null. Med. 50:1S-10S (2009); Eisenhauer et al., supra). In some embodiments, an anti-tumor response to a PD-1 antagonist is assessed using RECIST 1.1 criteria, bidimentional irRC or unidimensional irRC. In some embodiments, an anti-tumor response is any of SD, PR, CR, PFS, DFS. In some embodiments, a gene signature biomarker of the invention predicts whether a subject with a solid tumor is likely to achieve a PR or a CR.

"Bidimensional irRC" refers to the set of criteria described in Wolchok J D, et al. Guidelines for the evaluation of immune therapy activity in solid tumors: immune-related response criteria. *Clin Cancer Res.* 2009; 15(23): 7412-7420. These criteria utilize bidimensional tumor measurements of target lesions, which are obtained by multiplying the longest diameter and the longest perpendicular diameter (cm$^2$) of each lesion.

"Biotherapeutic agent" means a biological molecule, such as an antibody or fusion protein, that blocks ligand/receptor signaling in any biological pathway that supports tumor maintenance and/or growth or suppresses the anti-tumor immune response.

The terms "cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, hodgkin's lymphoma, non-hodgkin's lymphoma, acute myeloid leukemia (AML), multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer.

"CDR" or "CDRs" as used herein means complementarity determining region(s) in an immunoglobulin variable region, defined using the Kabat numbering system, unless otherwise indicated.

"Chemotherapeutic agent" is a chemical compound useful in the treatment of cancer. Classes of chemotherapeutic agents include, but are not limited to: alkylating agents, antimetabolites, kinase inhibitors, spindle poison plant alkaloids, cytoxic/antitumor antibiotics, topoisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists, anti-androgens, aromatase inhibitors, EGFR inhibitors, VEGF inhibitors, anti-sense oligonucleotides that that inhibit expression of genes implicated in abnormal cell proliferation or tumor growth. Chemotherapeutic agents useful in the treatment methods of the present invention include cytostatic and/or cytotoxic agents.

"Clinical Benefit" as applied herein to an outcome of treating a patient with a tumor with a PD-1 antagonist means any one or more of stable disease (SD), partial response (PR) and complete response (CR).

"Chothia" as used herein means an antibody numbering system described in Al-Lazikani et al., *JMB* 273:927-948 (1997).

"Comprising" or variations such as "comprise", "comprises" or "comprised of" are used throughout the specification and claims in an inclusive sense, i.e., to specify the presence of the stated features but not to preclude the presence or addition of further features that may materially enhance the operation or utility of any of the embodiments of the invention, unless the context requires otherwise due to express language or necessary implication.

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, if a gene signature score is defined as the composite RNA expression score for a set of genes that consists of a specified list of genes, the skilled artisan will understand that this gene signature score could include the RNA expression level determined for one or more additional genes, preferably no more than three additional genes, if such inclusion does not materially affect the predictive power.

"Framework region" or "FR" as used herein means the immunoglobulin variable regions excluding the CDR regions.

"Homology" refers to sequence similarity between two polypeptide sequences when they are optimally aligned. When a position in both of the two compared sequences is occupied by the same amino acid monomer subunit, e.g., if a position in a light chain CDR of two different Abs is occupied by alanine, then the two Abs are homologous at that position. The percent of homology is the number of homologous positions shared by the two sequences divided by the total number of positions compared ×100. For example, if 8 of 10 of the positions in two sequences are matched or homologous when the sequences are optimally aligned then the two sequences are 80% homologous. Generally, the comparison is made when two sequences are aligned to give maximum percent homology. For example, the comparison can be performed by a BLAST algorithm wherein the parameters of the algorithm are selected to give the largest match between the respective sequences over the entire length of the respective reference sequences.

The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, New York.

"Isolated antibody" and "isolated antibody fragment" refers to the purification status and in such context means the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Kabat" as used herein means an immunoglobulin alignment and numbering system pioneered by Elvin A. Kabat ((1991) Sequences of Proteins of Immunological Interest, 5th Ed. Public Health Service, National Institutes of Health, Bethesda, Md.).

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J Mol. Biol. 222: 581-597, for example. See also Presta (2005) J. Allergy Clin. Immunol. 116:731.

"Non-responder patient" when referring to a specific anti-tumor response to treatment with a PD-1 antagonist, means the patient did not exhibit the anti-tumor response. In an embodiment, the anti-tumor response is clinical benefit and a non-responder patient is one who did not achieve any clinical benefit. In another embodiment, the anti-tumor response is PR and a non-responder patient did not achieve a PR.

"Oligonucleotide" refers to a nucleic acid that is usually between 5 and 100 contiguous bases in length, and most frequently between 10-50, 10-40, 10-30, 10-25, 10-20, 15-50, 15-40, 15-30, 15-25, 15-20, 20-50, 20-40, 20-30 or 20-25 contiguous bases in length.

"Patient" refers to any single human subject for which therapy is desired or who is participating in a clinical trial, epidemiological study or used as a control.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the various aspects and embodiments of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in the any of the various aspects and embodiments of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the various aspects and embodiments of the present invention, are described in U.S. Pat. No. 7,521,051, U.S. Pat. No. 8,008,449, and U.S. Pat. No. 8,354,509. Specific anti-human PD-1 mAbs useful as the PD-1 antagonist various aspects and embodiments of the present invention include: pembrolizumab, a humanized IgG4 mAb with the structure described in WHO Drug Information, Vol. 27, No. 2, pages 161-162 (2013), nivolumab (BMS-936558), a human IgG4 mAb with the structure described in WHO Drug Information, Vol. 27, No. 1, pages 68-69 (2013); pidilizumab (CT-011, also known as hBAT or hBAT-1); and the humanized antibodies h409A11, h409A16 and h409A17, which are described in WO2008/156712.

Examples of mAbs that bind to human PD-L1, and useful in any of the various aspects and embodiments of the present invention, are described in WO2013/019906, WO2010/077634 A1 and U.S. Pat. No. 8,383,796. Specific anti-human PD-L1 mAbs useful as the PD-1 antagonist in the various aspects and embodiments of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the various aspects and embodiments of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Additional PD-1 antagonists useful in any of the various aspects and embodiments of the present invention include a pembrolizumab biosimilar or a pembrolizumab variant.

As used herein "pembrolizumab biosimilar" means a biological product that (a) is marketed by an entity other than Merck and Co., Inc. or a subsidiary thereof and (b) is approved by a regulatory agency in any country for marketing as a pembrolizumab biosimilar. In an embodiment, a pembrolizumab biosimilar comprises a pembrolizumab variant as the drug substance. In an embodiment, a pembrolizumab biosimilar has the same amino acid sequence as pembrolizumab.

As used herein, a "pembrolizumab variant" means a monoclonal antibody which comprises heavy chain and light chain sequences that are identical to those in pembrolizumab, except for having three, two or one conservative amino acid substitutions at positions that are located outside of the light chain CDRs and six, five, four, three, two or one conservative amino acid substitutions that are located outside of the heavy chain CDRs, e.g, the variant positions are located in the FR regions or the constant region. In other words, pembrolizumab and a pembrolizumab variant comprise identical CDR sequences, but differ from each other due to having a conservative amino acid substitution at no more than three or six other positions in their full length light and heavy chain sequences, respectively. A pembrolizumab variant is substantially the same as pembrolizumab with respect to the following properties: binding affinity to PD-1 and ability to block the binding of each of PD-L1 and PD-L2 to PD-1.

"Post-dose" as used herein refers to a time point following the administration of a first dose of a PD-1 antagonist to a patient. Thus, a "post-dose blood sample" means the sample is collected from the patient after the patient has been administered a first dose of the PD-1 antagonist. Similarly, administering a "post-dose treatment regimen" to a patient means a treatment regimen that is initiated after the patient was treated with a first dose of a PD-1 antagonist to a patient. In an embodiment, the "post-dose" time point refers to an action to be taken after a subsequent dose of the PD-1 antagonist, e.g., a second, third or fourth dose. In an embodiment, the time point for collecting a post-dose blood sample after the first dose is no sooner than one week after the first dose, and is typically between about two weeks and about four weeks after the first dose or about three weeks after the first dose.

"Probe" as used herein means an oligonucleotide that is capable of specifically hybridizing under stringent hybridization conditions to a transcript expressed by a gene of interest listed in any of Tables 1, 2, 3 and 4, and in some embodiments, specifically hybridizes under stringent hybridization conditions to the target region listed in Table Table 4 for the gene of interest.

"RECIST 1.1 Response Criteria" as used herein means the definitions set forth in Eisenhauer et al., E. A. et al., Eur. J Cancer 45:228-247 (2009) for target lesions or nontarget lesions, as appropriate based on the context in which response is being measured.

"Reference OxPhos gene signature score" as used herein means the score for an OxPhos gene signature of interest that has been determined to divide at least the majority of responders from at least the majority of non-responders in a reference population of patients who have the same tumor type as the test patient and who have been treated with a PD-1 antagonist. Preferably, at least any of 60%, 70%, 80%, or 90% of responders in the reference population will have a gene signature score that is lower than the selected reference score, while the OxPhos gene signature score for at least any of 60%, 70% 80%, 90% or 95% of the non-responders in the reference population will be greater than the selected reference score. In some embodiments, the negative predictive value of the reference score is greater than the positive predictive value. In some embodiments, responders in the reference population are defined as subjects who achieved a partial response (PR) or complete response (CR) as measured by RECIST 1.1 criteria and non-responders are defined as not achieving any RECIST 1.1 clinical response. In some embodiments, subjects in the reference population were treated with substantially the same anti-PD-1 therapy as that being considered for the test subject, i.e., administration of the same PD-1 antagonist using the same or a substantially similar dosage regimen.

"Sample" when referring to a sample of blood, tumor or any other biological material referenced herein, means a sample that has been removed from the subject; thus, none of the testing methods described herein are performed in or on the subject.

"Sustained response" means a sustained therapeutic effect after cessation of treatment with a PD-1 antagonist. In some embodiments, the sustained response has a duration that is at least the same as the treatment duration, or at least 1.5, 2.0, 2.5 or 3 times longer than the treatment duration.

"Treat" or "treating" a cancer as used herein means to administer a PD-1 antagonist other therapeutic agent to a subject having a cancer, or diagnosed with a cancer, to achieve at least one positive therapeutic effect, such as for example, reduced number of cancer cells, reduced tumor size, reduced rate of cancer cell infiltration into peripheral organs, or reduced rate of tumor metastasis or tumor growth. Positive therapeutic effects in cancer can be measured in a number of ways (See, W. A. Weber, J. Null. Med. 50:1S-10S (2009); Eisenhauer et al., supra). In some embodiments, response to a PD-1 antagonist is assessed using RECIST 1.1 criteria or irRC. In some embodiments, the treatment achieved by a therapeutically effective amount of a PD-1 antagonist is any of PR, CR, PFS, DFS, OR or OS. In some embodiments, a gene signature biomarker of the invention predicts whether a subject with a solid tumor is likely to achieve a PR or a CR. The dosage regimen of a therapy described herein that is effective to treat a cancer patient may vary according to factors such as the disease state, age, and weight of the patient, and the ability of the therapy to elicit an anti-cancer response in the subject. While an embodiment of the treatment method, medicaments and uses of the present invention may not be effective in achieving a positive therapeutic effect in every subject, it should do so in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Tumor burden" also referred to as "tumor load", refers to the total amount of tumor material distributed throughout the body. Tumor burden refers to the total number of cancer cells or the total size of tumor(s), throughout the body, including lymph nodes and bone narrow. Tumor burden can be determined by a variety of methods known in the art, such as, e.g. by measuring the dimensions of tumor(s) upon removal from the subject, e.g., using calipers, or while in the body using imaging techniques, e.g., ultrasound, bone scan, computed tomography (CT) or magnetic resonance imaging (MRI) scans.

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

"Variable regions" or "V region" as used herein means the segment of IgG chains which is variable in sequence between different antibodies. It extends to Kabat residue 109 in the light chain and 113 in the heavy chain.

II. Utility of Gene Signature Biomarkers of the Invention

The blood-based gene signatures described herein are useful to identify cancer patients who are most likely to achieve a clinical benefit from treatment with a PD-1 antagonist. This utility supports the use of these blood-based signatures in a variety of research and commercial applications, including but not limited to, clinical trials of PD-1 antagonists in which patients are selected on the basis of their baseline OxPhos gene signature score or their post-dose PD-L1 or IFNG gene signature score, diagnostic methods and products for determining a patient's PD-L1, IFNG, or OxPhos gene signature score or for classifying a patient as positive or negative for a baseline or on treatment gene signature biomarker, personalized treatment methods which involve tailoring a patient's drug therapy based on the patient's score for a blood-based gene signature, as well as pharmaceutical compositions and drug products comprising a PD-1 antagonist for use in treating a cancer in patients with a positive test for a baseline or on treatment biomarker described herein.

The utility of any of the applications claimed herein does not require that 100% of the patients who test positive for a biomarker of the invention achieve an anti-tumor response to a PD-1 antagonist; nor does it require a diagnostic method or kit to have a specific degree of specificity or sensitivity in determining the presence or absence of a biomarker in every subject, nor does it require that a diagnostic method claimed herein be 100% accurate in predicting for every subject whether the subject is likely to have a beneficial response to a PD-1 antagonist. Thus, the inventors herein intend that the terms "determine", "determining" and "predicting" should not be interpreted as requiring a definite or certain result; instead these terms should be construed as meaning either that a claimed method provides an accurate result for at least the majority of subjects or that the result or prediction for any given subject is more likely to be correct than incorrect.

Preferably, the accuracy of the result provided by a diagnostic method of the invention is one that a skilled artisan or regulatory authority would consider suitable for the particular application in which the method is used.

Similarly, the utility of the claimed drug products and treatment methods does not require that the claimed or desired effect is produced in every cancer patient; all that is required is that a clinical practitioner, when applying his or her professional judgment consistent with all applicable norms, decides there is a reasonable chance of achieving the claimed effect of treating a given patient according to the claimed method or with the claimed composition or drug product.

A. Testing for Biomarkers of the Invention

A score for a blood-based gene signature is determined using a blood sample collected from a patient with a tumor. The tumor may be primary or recurrent, and may be of any type (as described above), any stage (e.g., Stage I, II, III, or IV or an equivalent of other staging system), and/or histology. The subject may be of any age, gender, treatment history and/or extent and duration of remission.

In an embodiment, whole blood is collected using PAXgene® Blood RNA Tubes from PreAnalytiX® GmbH (Hombrechtikon, Switzerland). Total intracellular RNA may be isolated from the blood sample using a number of methods known in the art and commercially available reagent kits, including PAXgene® Blood RNA kits from PreAnalytiX® GmbH (Hombrechtikon, Switzerland) and TruSeq Stranded Total RNA with Ribo-Zero Globin kits from Illumina (San Diego, Calif.).

Once total RNA has been obtained from the blood sample, the RNA is analyzed to quantitate the expression level of each of the genes that comprise the particular gene signature to be scored, e.g. any of the gene signatures listed in Table 1, 2 and 3. The phrase "determine the expression level of a gene" as used herein refers to detecting and quantifying RNA transcribed from that gene. The term "RNA transcript" includes mRNA transcribed from the gene, and/or specific spliced variants thereof and/or fragments of such mRNA and spliced variants. In some embodiments, the RNA transcripts to be quantified are the transcripts listed in Table 1 or Table 2 for one of the gene signatures listed therein.

Persons skilled in the art are also aware of several methods useful for detecting and quantifying the level of RNA transcripts within RNA isolated from whole blood. Quantitative detection methods include, but are not limited to, arrays (i.e., microarrays), quantitative real time PCR (RT-PCR), multiplex assays, nuclease protection assays, and Northern blot analyses. Generally, such methods employ labeled probes that are complimentary to a portion of each transcript to be detected. Probes for use in these methods can be readily designed based on the known sequences of the genes and the transcripts expressed thereby. In some embodiments, the probes are designed to hybridize to each of the gene signature transcripts for the gene signature listed in Table 1A or Table 2B. Suitable labels for the probes are well-known and include, e.g., fluorescent, chemilumnescent and radioactive labels.

In some embodiments, assaying a blood sample for a gene signature of the invention employs detection and quantification of RNA levels in real-time using nucleic acid sequence based amplification (NASBA) combined with molecular beacon detection molecules. NASBA is described, e.g., in Compton J., *Nature* 350 (6313):91-92 (1991). NASBA is a single-step isothermal RNA-specific amplification method. Generally, the method involves the following steps: RNA template is provided to a reaction mixture, where the first primer attaches to its complementary site at the 3' end of the template; reverse transcriptase synthesizes the opposite, complementary DNA strand; RNAse H destroys the RNA template (RNAse H only destroys RNA in RNA-DNA hybrids, but not single-stranded RNA); the second primer attaches to the 3' end of the DNA strand, and reverse transcriptase synthesizes the second strand of DNA; and T7 RNA polymerase binds double-stranded DNA and produces a complementary RNA strand which can be used again in step 1, such that the reaction is cyclic.

In other embodiments, the assay format is a flap endonuclease-based format, such as the Invader™ assay (Third Wave Technologies). In the case of using the invader method, an invader probe containing a sequence specific to the region 3' to a target site, and a primary probe containing a sequence specific to the region 5' to the target site of a template and an unrelated flap sequence, are prepared. Cleavase is then allowed to act in the presence of these probes, the target molecule, as well as a FRET probe containing a sequence complementary to the flap sequence and an auto-complementary sequence that is labeled with both a fluorescent dye and a quencher. When the primary probe hybridizes with the template, the 3' end of the invader probe penetrates the target site, and this structure is cleaved by the Cleavase resulting in dissociation of the flap. The flap binds to the FRET probe and the fluorescent dye portion is cleaved by the Cleavase resulting in emission of fluorescence.

In yet other embodiments, the assay format employs direct mRNA capture with branched DNA (QuantiGene™, Panomics) or Hybrid Capture™ (Digene).

One example of an array technology suitable for use in measuring expression of the genes in a gene signature is the ArrayPlate™ assay technology sold by HTG Molecular, Tucson Ariz., and described in Martel, R. R., et al., Assay and Drug Development Technologies 1(1):61-71, 2002. In brief, this technology combines a nuclease protection assay with array detection. Cells in microplate wells are subjected to a nuclease protection assay. Cells are lysed in the presence of probes that bind targeted mRNA species. Upon addition of SI nuclease, excess probes and unhybridized mRNA are degraded, so that only mRNA:probe duplexes remain. Alkaline hydrolysis destroys the mRNA component of the duplexes, leaving probes intact. After the addition of a neutralization solution, the contents of the processed cell culture plate are transferred to another ArrayPlate™ called a programmed ArrayPlate™. ArrayPlates™ contain a 16-element array at the bottom of each well. Each array element comprises a position-specific anchor oligonucleotide that remains the same from one assay to the next. The binding specificity of each of the 16 anchors is modified with an oligonucleotide, called a programming linker oligonucleotide, which is complementary at one end to an anchor and at the other end to a nuclease protection probe. During a hybridization reaction, probes transferred from the culture plate are captured by immobilized programming linker. Captured probes are labeled by hybridization with a detection linker oligonucleotide, which is in turn labeled with a detection conjugate that incorporates peroxidase. The enzyme is supplied with a chemiluminescent substrate, and the enzyme-produced light is captured in a digital image. Light intensity at an array element is a measure of the amount of corresponding target mRNA present in the original cells.

By way of further example, DNA microarrays can be used to measure gene expression. In brief, a DNA microarray, also referred to as a DNA chip, is a microscopic array of DNA fragments, such as synthetic oligonucleotides, disposed in a defined pattern on a solid support, wherein they are amenable to analysis by standard hybridization methods (see Schena, *BioEssays* 18:427 (1996)). Exemplary microarrays and methods for their manufacture and use are set forth in T. R. Hughes et al., *Nature Biotechnology* 9:342-347 (2001). A number of different microarray configurations and methods for their production are known to those of skill in the art and are disclosed in U.S. Pat. Nos. 5,242,974; 5,384,261; 5,405,783; 5,412,087; 5,424,186; 5,429,807; 5,436,327; 5,445,934; 5,556,752; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,624,711; 5,700,637; 5,744,305; 5,770,456; 5,770,722; 5,837,832; 5,856,101; 5,874,219; 5,885,837; 5,919,523; 6,022,963; 6,077,674; and U.S. Pat. No. 6,156,501; Shena, et al., *Tibtech* 6:301-306, 1998; Duggan, et al., *Nat. Genet.* 2:10-14, 1999; Bowtell, et al., *Nat. Genet.* 21:25-32, 1999; Lipshutz, et al., *Nat. Genet.* 21:20-24, 1999; Blanchard, et al., *Biosensors and Bioelectronics* 77:687-90, 1996; Maskos, et al., *Nucleic Acids Res.* 2:4663-69, 1993; and Hughes, et al., *Nat. Biotechnol.* 79:342-347, 2001. Patents describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,848,659; and 5,874,219; the disclosures of which are herein incorporated by reference.

In one embodiment, an array of oligonucleotides may be synthesized on a solid support. Exemplary solid supports include glass, plastics, polymers, metals, metalloids, ceramics, organics, etc. Using chip masking technologies and photoprotective chemistry, it is possible to generate ordered arrays of nucleic acid probes. These arrays, which are known, for example, as "DNA chips" or very large scale immobilized polymer arrays ("VLSIPS®" arrays), may include millions of defined probe regions on a substrate having an area of about 1 $cm^2$ to several $cm^2$, thereby incorporating from a few to millions of probes (see, e.g., U.S. Pat. No. 5,631,734).

To compare expression levels, labeled nucleic acids may be contacted with the array under conditions sufficient for binding between the target nucleic acid and the probe on the array. In one embodiment, the hybridization conditions may be selected to provide for the desired level of hybridization specificity; that is, conditions sufficient for hybridization to occur between the labeled nucleic acids and probes on the microarray.

Hybridization may be carried out in conditions permitting essentially specific hybridization. The length and GC content of the nucleic acid will determine the thermal melting point and thus, the hybridization conditions necessary for obtaining specific hybridization of the probe to the target nucleic acid. These factors are well known to a person of skill in the art, and may also be tested in assays. An extensive guide to nucleic acid hybridization may be found in Tijssen, et al. (Laboratory Techniques in Biochemistry and Molecular Biology, Vol. 24: Hybridization With Nucleic Acid Probes, P. Tijssen, ed.; Elsevier, N.Y. (1993)). The methods described above will result in the production of hybridization patterns of labeled target nucleic acids on the array surface. The resultant hybridization patterns of labeled nucleic acids may be visualized or detected in a variety of ways, with the particular manner of detection selected based on the particular label of the target nucleic acid. Representative detection means include scintillation counting, autoradiography, fluorescence measurement, calorimetric measurement, light emission measurement, light scattering, and the like.

One such method of detection utilizes an array scanner that is commercially available (Affymetrix, Santa Clara, Calif.), for example, the 417® Arrayer, the 418® Array Scanner, or the Agilent Gene Array® Scanner. This scanner is controlled from a system computer with an interface and easy-to-use software tools. The output may be directly imported into or directly read by a variety of software applications. Exemplary scanning devices are described in, for example, U.S. Pat. Nos. 5,143,854 and 5,424,186.

A preferred assay method to measure biomarker transcript abundance includes using the nCounter® Analysis System marketed by NanoString® Technologies (Seattle, Wash. USA). This system, which is described by Geiss et al., *Nature Biotechnol.* 2(3):317-325 (2008), utilizes a pair of probes, namely, a capture probe and a reporter probe, each comprising a 35- to 50-base sequence complementary to the transcript to be detected. The capture probe additionally includes a short common sequence coupled to an immobilization tag, e.g. an affinity tag that allows the complex to be immobilized for data collection. The reporter probe additionally includes a detectable signal or label, e.g. is coupled to a color-coded tag. Following hybridization, excess probes are removed from the sample, and hybridized probe/target complexes are aligned and immobilized via the affinity or other tag in a cartridge. The samples are then analyzed, for example using a digital analyzer or other processor adapted for this purpose. Generally, the color-coded tag on each transcript is counted and tabulated for each target transcript to yield the expression level of each transcript in the sample. This system allows measuring the expression of hundreds of unique gene transcripts in a single multiplex assay using capture and reporter probes designed by NanoString.

In another preferred assay method, the TrueSeq Stranded Total RNA with Ribo-Zero Globin kit marketed by Illumina (San Diego, Calif.) is used to isolate RNA isolated from stabilized, whole blood samples (e.g., collected using PAXgene® Blood RNA Tubes) and the isolated RNA is sequenced on an Illumina Next-Generation Sequencing (NGS) platform.

In measuring expression of the genes in a gene signature described herein, the absolute expression of each of the genes in total RNA isolated from a blood sample is compared to a control; for example, the control can be the average level of expression of each of the genes, respectively, in a pool of subjects. To increase the sensitivity of the comparison, however, the expression level values are preferably transformed in a number of ways.

Raw expression values of the genes in a gene signature described herein may be normalized by any of the following: quantile normalization to a common reference distribution, by the mean RNA levels of a set of housekeeping genes, by global normalization relying on percentile, e.g., $75^{th}$ percentile, or other biologically relevant normalization approaches known to those skilled in the art.

For example, the expression level of each gene can be normalized by the average RNA expression level of all of the genes in the gene signature, or by the average expression level of a set of normalization genes, or by the average expression level of the signature genes and a set of normalization genes. Thus, in one embodiment, the genes in a gene signature and normalization gene set are represented by a set of probes, and the RNA expression level of each of the signature genes is normalized by the mean or median expression level across all of the represented genes, i.e., across all signature and normalization genes. In a specific embodiment, normalization of a signature gene expression measurement is carried out by dividing the measured RNA level by the median or mean level of RNA expression of all of the genes in Table 4. In another specific embodiment, the RNA expression levels of each signature gene is normalized by dividing the measured RNA level by the mean or median level of expression of a set of normalization genes. In a specific embodiment, the normalization genes comprise housekeeping genes.

The sensitivity of a gene signature score may be increased if the expression levels of individual genes in the gene signature are compared to the expression of the same genes in a plurality of blood samples combined together. Preferably, the comparison is to the mean or median expression level of each signature gene in the combined samples. This has the effect of accentuating the relative differences in expression between genes in the individual sample and in the combined samples, making comparisons more sensitive and more likely to produce meaningful results than the use of absolute expression levels alone. The expression level data may be transformed in any convenient way; preferably, the expression level data for all genes is log transformed before means or medians are taken.

In performing comparisons of an individual sample to combined samples, two approaches may be used. First, the expression levels of the signature genes in the sample may be compared to the expression level of those genes in the combined samples, where nucleic acid derived from the sample and nucleic acid derived from the combined samples are hybridized during the course of a single experiment. Such an approach requires that a new amount of nucleic acid from the combined samples be generated for each comparison or limited numbers of comparisons, and is therefore limited by the amount of nucleic acid available. Alternatively, and preferably, the expression levels in a sample combination, whether normalized and/or transformed or not, are stored on a computer, or on computer-readable media, to be used in comparisons to the individual expression level data from the sample (i.e., single-channel data).

When comparing a subject's blood sample with a standard or control, the expression value of a particular gene in the sample is compared to the expression value of that gene in the standard or control. For each gene in a gene signature of the invention, the log(10) ratio is created for the expression value in the individual sample relative to the standard or control. A score for a gene signature of interest is calculated by determining the mean log(10) ratio of the genes in that signature.

It will be recognized by those skilled in the art that other differential expression values, besides log(10) ratio, may be used for calculating a signature score, as long as the value represents an objective measurement of transcript abundance of the genes. Examples include, but are not limited to: xdev, error-weighted log (ratio), and mean subtracted log (intensity).

Once normalized RNA expression values are obtained, signature scores may be calculated in several ways. Predictive scores may be derived by using all of the genes in the signature as a set of input covariates to multivariate statistical models that will determine signature scores using the fitted model coefficients, for example the linear predictor in a logistic or Cox regression. One specific example of a multivariate strategy is the use of elastic net modeling (Zou & Hastie, 2005, *J.R. Statist Soc. B* 67(2): 301-320; Simon et al., 2011, *J. Statistical Software* 39(5): 1-13), which is a penalized regression approach that uses a hybrid between the penalties of the lasso and ridge regression, with cross-validation to select the penalty parameters. Because the RNA expression levels for most, if not all, of the signature genes are expected to be predictive, in one embodiment the L1 penalty parameter may be set very low, effectively running a ridge regression.

A multivariate approach may use a meta-analysis that combines data across cancer indications or may be applied within a single cancer indication. In either case, analyses would use the normalized intra-tumoral RNA expression levels of the signature genes as the input predictors, with anti-tumor response as the dependent variable. The result of such an analysis algorithmically defines the signature score for blood samples from the patients used in the model fit, as well as for blood samples from future patients, as a numeric combination of the multiplication co-efficients for the normalized RNA expression levels of the signature genes that is expected to be predictive of anti-tumor response. The gene signature score is determined by the linear combination of the signature genes, as dictated by the final estimated values of the elastic net model coefficients at the selected values of the tuning parameters. Specifically, for a given blood sample and gene signature, the estimated coefficient for each gene in the signature is multiplied by the normalized RNA expression level of that gene in the blood sample and then the resulting products are summed to yield the signature score for that blood sample. Multivariate model-based strategies other than elastic net could also be used to determine a gene signature score.

An alternative to such model-based signature scores would be to use a simple averaging approach, e.g., the signature score for each blood sample would be defined as the average of that sample's normalized RNA expression levels for each signature gene.

In some embodiments, expression of signature genes in total RNA isolated from a blood sample is detected using RNA-Seq technology from Illumina (San Diego, Calif.). The blood sample is processed to remove globin mRNA and cytoplasmic and mitochondrial ribosomal RNA, which may be achieved using Illumina's TruSeq Stranded Total RNA with Ribo-Zero Globin kit. The gene expression data generated from sequencing the remaining total RNA is processed as follows. Fragments Per Kilobase of exon per Million fragments mapped (FPKM) values are transformed using log 10(0.01+FPKM) and subsequently normalized by the upper quartile measured over approximately 20,000 transcripts corresponding to protein-coding genes. This transformation generates values that are close to log 10 for large input values and close to linear scale for low values (<1), with the added benefit of yielding zero values for zero input values. Genes with maximum count below 10 are deemed not reliably detected and thus filtered out.

In some embodiments, gene expression is detected using the nCounter® Analysis System marketed by NanoString® Technologies, and the raw expression values are normalized by performing quantile normalization relative to the reference distribution and subsequent log 10-transformation. The reference distribution is generated by pooling reported (i.e., raw) counts for the test sample and one or more other test or control samples (preferably at least 2 samples, more preferably at least any of 4, 8 or 16 samples) after excluding values for positive and negative control probes. The signature score is then calculated as the arithmetic mean of normalized values for each of the genes in the gene signature, e.g., for the IFNG ten-gene signature, the signature score equals the arithmetic mean of normalized RNA expression values for each of IFNG, STAT1, CCR5, CXCL9, PRF1, HLA-DRA, CXCL10, CXCL11, IDO1 and GZMA. In an embodiment, the reference distribution is generated from raw expression counts in a pool of total RNA samples (e.g., test plus control samples) for target transcripts of all of the 680 genes listed in Table 4, or a subset thereof.

TABLE 4

Set of 680 Normalization Genes

| Gene Id | Target Transcript NCBI Accession # | Exemplary Target Region |
|---|---|---|
| AAMP | NM_001087.3 | 412-512 |
| ABCB1 | NM_000927.3 | 3910-4010 |
| ABCF1 | NM_001090.2 | 850-950 |
| ADIPOQ | NM_004797.2 | 790-890 |
| ADORA2A | NM_000675.3 | 1095-1195 |
| AGGF1 | NM_018046.3 | 35-135 |
| ALAS1 | NM_000688.4 | 1615-1715 |
| ALB | NM_000477.5 | 855-955 |
| AMICA1 | NM_153206.2 | 620-720 |
| ANTXR1 | NM_018153.3 | 455-555 |
| ANXA4 | NM_001153.2 | 430-530 |
| AP1M2 | NM_005498.4 | 78-178 |
| AP1S2 | NM_003916.3 | 728-828 |
| AREG | NM_001657.2 | 547-647 |

TABLE 4-continued

Set of 680 Normalization Genes

| Gene Id | Target Transcript NCBI Accession # | Exemplary Target Region |
|---|---|---|
| ARG1 | NM_000045.2 | 505-605 |
| ARG2 | NM_001172.3 | 1150-1250 |
| ASCL2 | NM_005170.2 | 1470-1570 |
| ATP6V0D2 | NM_152565.1 | 480-580 |
| ATP8B4 | NM_024837.2 | 95-195 |
| AURKA | NM_003600.2 | 405-505 |
| AURKB | NM_004217.2 | 615-715 |
| AXL | NM_021913.2 | 2190-2290 |
| B2M | NM_004048.2 | 235-335 |
| B3GAT1 | NM_018644.3 | 2388-2488 |
| BATF | NM_006399.3 | 293-393 |
| BCAM | NM_005581.3 | 156-256 |
| BCL11A | NM_022893.3 | 735-835 |
| BCL11B | NM_022898.1 | 3420-3520 |
| BCL2 | NM_000657.2 | 947-1047 |
| BCL6 | NM_138931.1 | 505-605 |
| BIM | NM_138621.4 | 257-357 |
| BIRC5 | NM_001168.2 | 1215-1315 |
| BLNK | NM_013314.2 | 930-1030 |
| BNC1 | NM_001717.3 | 2500-2600 |
| BRAF | NM_004333.3 | 565-665 |
| BRCA1 | NM_007305.2 | 1275-1375 |
| BRCA2 | NM_000059.3 | 115-215 |
| BST1 | NM_004334.2 | 710-810 |
| BST2 | NM_004335.2 | 560-660 |
| BTLA | NM_181780.2 | 305-405 |
| BTN1A1 | NM_001732.2 | 756-856 |
| BTN2A1 | NM_001197234.1 | 1088-1188 |
| BTN2A2 | NM_181531.2 | 540-640 |
| BTN3A1 | NM_001145009.1 | 1162-1262 |
| BTN3A2 | NM_001197246.1 | 940-1040 |
| BTN3A3 | NM_197974.2 | 1086-1186 |
| BTNL2 | NM_019602.1 | 961-1061 |
| BTNL8 | NM_001040462.2 | 900-1000 |
| BTNL9 | NM_152547.4 | 1986-2086 |
| BUB1 | NM_004336.2 | 100-200 |
| C10orf54 | NM_022153.1 | 1955-2055 |
| C14orf102 | NM_017970.3 | 3236-3336 |
| C1orf210 | NM_182517.2 | 966-1066 |
| CADM1 | NM_014333.3 | 2840-2940 |
| CASP3 | NM_032991.2 | 685-785 |
| CASP8 | NM_001228.4 | 301-401 |
| CCL19 | NM_006274.2 | 401-501 |
| CCL21 | NM_002989.2 | 180-280 |
| CCL24 | NM_002991.2 | 18-118 |
| CCL27 | NM_006664.2 | 304-404 |
| CCL3 | NM_002983.2 | 159-259 |
| CCL4 | NM_002984.2 | 35-135 |
| CCL5 | NM_002985.2 | 280-380 |
| CCL8 | NM_005623.2 | 689-789 |
| CCNB1 | NM_031966.2 | 715-815 |
| CCNB2 | NM_004701.2 | 980-1080 |
| CCR1 | NM_001295.2 | 535-635 |
| CCR2 | NM_001123041.2 | 743-843 |
| CCR3 | NM_001837.2 | 980-1080 |
| CCR4 | NM_005508.4 | 35-135 |
| CCR5 | NM_000579.1 | 2730-2830 |
| CCR6 | NM_031409.2 | 935-1035 |
| CCR7 | NM_001838.2 | 1610-1710 |
| CD14 | NM_000591.2 | 885-985 |
| CD160 | NM_007053.2 | 500-600 |
| CD163 | NM_004244.4 | 1630-1730 |
| CD1D | NM_001766.3 | 1428-1528 |
| CD2 | NM_001767.3 | 687-787 |
| CD200 | NM_005944.5 | 665-765 |
| CD200R1 | NM_138806.3 | 142-242 |
| CD207 | NM_015717.2 | 995-1095 |
| CD209 | NM_021155.2 | 1532-1632 |
| CD22 | NM_001771.2 | 2515-2615 |
| CD226 | NM_006566.2 | 163-263 |
| CD24 | NM_013230.2 | 95-195 |
| CD244 | NM_016382.2 | 1150-1250 |
| CD247 | NM_198053.1 | 1490-1590 |
| CD27 | NM_001242.4 | 330-430 |
| CD274 | NM_014143.3 | 1245-1345 |

TABLE 4-continued

Set of 680 Normalization Genes

| Gene Id | Target Transcript NCBI Accession # | Exemplary Target Region |
|---|---|---|
| CD276 | NM_001024736.1 | 2120-2220 |
| CD28 | NM_001243078.1 | 2065-2165 |
| CD300A | NM_007261.3 | 902-1002 |
| CD300E | NM_181449.1 | 330-430 |
| CD300LB | NM_174892.2 | 1530-1630 |
| CD300LF | NM_139018.3 | 774-874 |
| CD33 | NM_001177608.1 | 730-830 |
| CD37 | NM_001774.2 | 844-944 |
| CD38 | NM_001775.2 | 1035-1135 |
| CD3D | NM_000732.4 | 110-210 |
| CD3E | NM_000733.2 | 75-175 |
| CD3G | NM_000073.2 | 515-615 |
| CD4 | NM_000616.4 | 975-1075 |
| CD40 | NM_001250.4 | 1265-1365 |
| CD40LG | NM_000074.2 | 1225-1325 |
| CD44 | NM_001001392.1 | 429-529 |
| CD47 | NM_001777.3 | 897-997 |
| CD48 | NM_001778.2 | 270-370 |
| CD5 | NM_014207.2 | 1295-1395 |
| CD52 | NM_001803.2 | 200-300 |
| CD55 | NM_000574.3 | 101-201 |
| CD59 | NM_000611.4 | 730-830 |
| CD6 | NM_006725.3 | 1280-1380 |
| CD68 | NM_001251.2 | 1140-1240 |
| CD69 | NM_001781.1 | 460-560 |
| CD7 | NM_006137.6 | 440-540 |
| CD70 | NM_001252.2 | 190-290 |
| CD72 | NM_001782.2 | 1044-1144 |
| CD74 | NM_001025159.1 | 964-1064 |
| CD79A | NM_001783.3 | 695-795 |
| CD80 | NM_005191.3 | 1288-1388 |
| CD84 | NM_001184879.1 | 1775-1875 |
| CD86 | NM_175862.3 | 1265-1365 |
| CD8a | NM_001768.5 | 1320-1420 |
| CD8B | NM_172099.2 | 439-539 |
| CD9 | NM_001769.2 | 405-505 |
| CD96 | NM_005816.4 | 1355-1455 |
| CD97 | NM_078481.2 | 1370-1470 |
| CDC42SE1 | NM_001038707.1 | 2625-2725 |
| CDCA2 | NM_152562.2 | 1750-1850 |
| CDCA3 | NM_031299.4 | 825-925 |
| CDH1 | NM_004360.2 | 1230-1330 |
| CDH11 | NM_001797.2 | 1835-1935 |
| CDH17 | NM_004063.3 | 298-398 |
| CDH2 | NM_001792.3 | 941-1041 |
| CDH3 | NM_001793.4 | 3745-3845 |
| CDH5 | NM_001795.3 | 3405-3505 |
| CDKN1A | NM_000389.2 | 1975-2075 |
| CDKN2A | NM_000077.3 | 975-1075 |
| CDKN2C | NM_001262.2 | 1295-1395 |
| CDO1 | NM_001801.2 | 125-225 |
| CEACAM1 | NM_001712.3 | 2455-2555 |
| CENPA | NM_001809.3 | 265-365 |
| CHGA | NM_001275.3 | 292-392 |
| CHI3L1 | NM_001276.2 | 475-575 |
| CHI3L2 | NM_004000.2 | 1195-1295 |
| CIITA | NM_000246.3 | 470-570 |
| CLCA1 | NM_001285.3 | 2705-2805 |
| CLCA2 | NM_006536.5 | 2700-2800 |
| CLDN4 | NM_001305.3 | 1242-1342 |
| CLDN7 | NM_001307.3 | 175-275 |
| CLEC10A | NM_182906.2 | 430-530 |
| CLEC12A | NM_138337.5 | 768-868 |
| CLEC1B | NM_016509.3 | 649-749 |
| CLEC2D | NM_001004419.3 | 4565-4665 |
| CLEC3B | NM_003278.2 | 607-707 |
| CLEC4A | NM_194448.2 | 388-488 |
| CLEC4D | NM_080387.4 | 1575-1675 |
| CLEC4E | NM_014358.2 | 570-670 |
| CLEC5A | NM_013252.2 | 615-715 |
| CLEC6A | NM_001007033.1 | 342-442 |
| CLEC7A | NM_197954.2 | 55-155 |
| CLEC9A | NM_207345.2 | 480-580 |
| CLIP3 | NM_015526.1 | 2025-2125 |
| CMKLR1 | NM_004072.1 | 770-870 |
| CPD | NM_001304.4 | 2585-2685 |
| CRLF2 | NM_001012288.1 | 605-705 |
| CRTAM | NM_019604.2 | 555-655 |
| CSF1 | NM_000757.4 | 823-923 |
| CSF1R | NM_005211.2 | 3775-3875 |
| CSF2RB | NM_000395.2 | 3300-3400 |
| CSF3 | NM_000759.3 | 851-951 |
| CSPG4 | NM_001897.4 | 7642-7742 |
| CST6 | NM_001323.3 | 418-518 |
| CST7 | NM_003650.3 | 525-625 |
| CSTB | NM_000100.2 | 320-420 |
| CTAG1B | NM_001327.2 | 285-385 |
| CTLA4 | NM_005214.3 | 405-505 |
| CTNNB1 | NM_001904.3 | 2265-2365 |
| CTSB | NM_001908.3 | 595-695 |
| CTSG | NM_001911.2 | 160-260 |
| CTSL2 | NM_001333.3 | 2820-2920 |
| CTSS | NM_004079.3 | 685-785 |
| CTSZ | NM_001336.3 | 827-927 |
| CX3CL1 | NM_002996.3 | 140-240 |
| CX3CR1 | NM_001337.3 | 1040-1140 |
| CXCL1 | NM_001511.1 | 742-842 |
| CXCL10 | NM_001565.1 | 40-140 |
| CXCL11 | NM_005409.4 | 282-382 |
| CXCL13 | NM_006419.2 | 210-310 |
| CXCL14 | NM_004887.4 | 1125-1225 |
| CXCL2 | NM_002089.3 | 854-954 |
| CXCL3 | NM_002090.2 | 540-640 |
| CXCL9 | NM_002416.1 | 1975-2075 |
| CXCR2 | NM_001557.2 | 2055-2155 |
| CXCR3 | NM_001504.1 | 80-180 |
| CXCR6 | NM_006564.1 | 95-195 |
| CXCR7 | NM_020311.1 | 375-475 |
| DAB1 | NM_021080.3 | 772-872 |
| DAB2IP | NM_138709.1 | 222-322 |
| DAPK1 | NM_004938.2 | 355-455 |
| DCK | NM_000788.2 | 310-410 |
| DCT | NM_001922.3 | 1755-1855 |
| DDR1 | NM_001954.4 | 1342-1442 |
| DEF6 | NM_022047.3 | 2120-2220 |
| DEFB1 | NM_005218.3 | 40-140 |
| DEFB4A | NM_004942.2 | 97-197 |
| DGKZ | NM_001105540.1 | 2142-2242 |
| DIRAS3 | NM_004675.2 | 950-1050 |
| DOCK5 | NM_024940.6 | 630-730 |
| DPP4 | NM_001935.3 | 2700-2800 |
| DSC1 | NM_024421.2 | 3611-3711 |
| DSC2 | NM_024422.3 | 2200-2300 |
| DSG2 | NM_001943.3 | 235-335 |
| DSG3 | NM_001944.2 | 1630-1730 |
| DST | NM_001723.4 | 1870-1970 |
| DUSP1 | NM_004417.2 | 987-1087 |
| DUSP6 | NM_001946.2 | 1535-1635 |
| EBAG9 | NM_198120.1 | 407-507 |
| EBI3 | NM_005755.2 | 485-585 |
| ECSCR | NM_001077693.2 | 415-515 |
| EEF1G | NM_001404.4 | 1150-1250 |
| EFEMP1 | NM_004105.3 | 1642-1742 |
| EGF | NM_001963.3 | 3930-4030 |
| EGFR | NM_201282.1 | 360-460 |
| EGR2 | NM_000399.3 | 1891-1991 |
| ELF3 | NM_004433.4 | 1665-1765 |
| EMILIN2 | NM_032048.2 | 1445-1545 |
| EMR2 | NM_013447.2 | 6010-6110 |
| ENAH | NM_001008493.1 | 10855-10955 |
| ENTPD1 | NM_001098175.1 | 8830-8930 |
| EOMES | NM_005442.2 | 1670-1770 |
| EPCAM | NM_002354.1 | 415-515 |
| EPSTI1 | NM_001002264.1 | 610-710 |
| ERAP1 | NM_001040458.1 | 754-854 |
| ERBB2 | NM_004448.2 | 2380-2480 |
| ESR1 | NM_000125.2 | 2390-2490 |
| EZR | NM_003379.4 | 290-390 |
| FAM83B | NM_001010872.1 | 415-515 |
| FAP | NM_004460.2 | 1490-1590 |

TABLE 4-continued

Set of 680 Normalization Genes

| Gene Id | Target Transcript NCBI Accession # | Exemplary Target Region |
|---|---|---|
| FAS | NM_152876.1 | 1740-1840 |
| FASLG | NM_000639.1 | 625-725 |
| FCER1A | NM_002001.2 | 114-214 |
| FCGR2A | NM_021642.3 | 60-160 |
| FCGR2B | NM_001002273.1 | 870-970 |
| FCGR3A | NM_000569.6 | 1644-1744 |
| FCN1 | NM_002003.2 | 880-980 |
| FCRL1 | NM_052938.3 | 1685-1785 |
| FCRL3 | NM_052939.3 | 165-265 |
| FCRL4 | NM_031282.1 | 2055-2155 |
| FCRL5 | NM_031281.2 | 3654-3754 |
| FCRL6 | NM_001004310.2 | 930-1030 |
| FGF1 | NM_033137.1 | 315-415 |
| FLT1 | NM_002019.4 | 530-630 |
| FN1 | NM_212482.1 | 1776-1876 |
| FOLR1 | NM_000802.2 | 815-915 |
| FOLR2 | NM_000803.4 | 851-951 |
| FOLR3 | NM_000804.2 | 469-569 |
| FOLR4 | NM_001199206.1 | 542-642 |
| FOSL1 | NM_005438.2 | 280-380 |
| FOXP3 | NM_014009.3 | 1230-1330 |
| G6PD | NM_000402.2 | 1155-1255 |
| GAPDH | NM_002046.3 | 972-1072 |
| GAS6 | NM_000820.2 | 1339-1439 |
| GATA3 | NM_001002295.1 | 2835-2935 |
| GBP1 | NM_002053.1 | 2110-2210 |
| GCH1 | NM_000161.2 | 1910-2010 |
| GDF10 | NM_004962.2 | 1638-1738 |
| GFI1 | NM_005263.2 | 2235-2335 |
| GJB5 | NM_006783.4 | 488-588 |
| GJB6 | NM_006783.4 | 847-947 |
| GNLY | NM_006433.2 | 305-405 |
| GOLT1A | NM_198447.1 | 265-365 |
| GPLD1 | NM_001503.2 | 465-565 |
| GPR18 | NM_001098200.1 | 1060-1160 |
| GRAP2 | NM_004810.2 | 232-332 |
| GRB7 | NM_005310.2 | 1010-1110 |
| GUSB | NM_000181.1 | 1350-1450 |
| GZMA | NM_006144.2 | 155-255 |
| GZMB | NM_004131.3 | 540-640 |
| GZMK | NM_002104.2 | 700-800 |
| HAVCR1 | NM_001099414.1 | 968-1068 |
| HAVCR2 | NM_032782.3 | 955-1055 |
| HCLS1 | NM_005335.4 | 515-615 |
| HCST | NM_001007469.1 | 132-232 |
| HES4 | NM_001142467.1 | 557-657 |
| HGFAC | NM_001528.2 | 1377-1477 |
| HHLA2 | NM_007072.2 | 1430-1530 |
| HIF1A | NM_001530.3 | 1985-2085 |
| HLA-A | NM_002116.5 | 1000-1100 |
| HLA-B | NM_005514.6 | 937-1037 |
| HLA-C | NM_002117.4 | 895-995 |
| HLA-DPB1 | NM_002121.4 | 931-1031 |
| HLA-DQA1 | NM_002122.3 | 261-361 |
| HLA-DRA | NM_019111.3 | 335-435 |
| HLA-DRB1 | NM_002124.1 | 985-1085 |
| HLA-E | NM_005516.4 | 1204-1304 |
| HLA-F | NM_001098479.1 | 575-675 |
| HLA-G | NM_002127.4 | 1180-1280 |
| HMGA1 | NM_145904.1 | 871-971 |
| HMGB1 | NM_002128.4 | 208-308 |
| HNF1B | NM_000458.1 | 2000-2100 |
| HNRNPL | NM_001533.2 | 757-857 |
| HOPX | NM_001145460.1 | 1117-1217 |
| HPRT1 | NM_000194.1 | 240-340 |
| HSD3B7 | NM_001142777.1 | 2043-2143 |
| ICA1 | NM_001136020.1 | 145-245 |
| ICAM1 | NM_000201.2 | 2253-2353 |
| ICOS | NM_012092.2 | 640-740 |
| ICOSLG | NM_015259.4 | 1190-1290 |
| ID2 | NM_002166.4 | 505-605 |
| IDO1 | NM_002164.3 | 50-150 |
| IFI16 | NM_005531.1 | 2255-2355 |
| IFITM1 | NM_003641.3 | 482-582 |
| IFNG | NM_000619.2 | 970-1070 |
| IFNGR2 | NM_005534.3 | 799-899 |
| IGF1 | NM_000618.3 | 491-591 |
| IGJ | NM_144646.3 | 435-535 |
| IGSF6 | NM_005849.2 | 58-158 |
| IKZF2 | NM_016260.2 | 870-970 |
| IKZF3 | NM_183232.2 | 1176-1276 |
| IL10 | NM_000572.2 | 230-330 |
| IL10RA | NM_001558.2 | 150-250 |
| IL10RB | NM_000628.3 | 1760-1860 |
| IL13 | NM_002188.2 | 516-616 |
| IL18 | NM_001562.2 | 48-148 |
| IL18R1 | NM_003855.2 | 2025-2125 |
| IL2 | NM_000586.2 | 300-400 |
| IL21 | NM_021803.2 | 65-165 |
| IL22 | NM_020525.4 | 319-419 |
| IL23R | NM_144701.2 | 710-810 |
| IL27 | NM_145659.3 | 143-243 |
| IL27RA | NM_004843.2 | 2965-3065 |
| IL2RA | NM_000417.1 | 1000-1100 |
| IL2RB | NM_000878.2 | 1980-2080 |
| IL2RG | NM_000206.1 | 595-695 |
| IL-32 | NM_001012633.1 | 758-858 |
| IL4 | NM_000589.2 | 625-725 |
| IL6 | NM_000600.1 | 220-320 |
| IL7 | NM_000880.2 | 38-138 |
| IL7R | NM_002185.2 | 1610-1710 |
| ILDR1 | NM_175924.3 | 1672-1772 |
| ILDR2 | NM_199351.2 | 558-658 |
| ING1 | NM_005537.3 | 2690-2790 |
| ING2 | NM_001564.2 | 445-545 |
| INSR | NM_000208.1 | 525-625 |
| IQGAP3 | NM_178229.4 | 345-445 |
| IRF1 | NM_002198.1 | 510-610 |
| IRF2 | NM_002199.2 | 1375-1475 |
| IRF3 | NM_001571.5 | 1303-1403 |
| IRF4 | NM_002460.1 | 325-425 |
| IRF5 | NM_002200.3 | 1845-1945 |
| IRF6 | NM_006147.2 | 1430-1530 |
| IRF7 | NM_001572.3 | 1763-1863 |
| IRF8 | NM_002163.2 | 253-353 |
| ITGA1 | NM_181501.1 | 1875-1975 |
| ITGA2 | NM_002203.2 | 475-575 |
| ITGAE | NM_002208.4 | 3405-3505 |
| ITGAL | NM_002209.2 | 3905-4005 |
| ITGAM | NM_000632.3 | 515-615 |
| ITGAV | NM_002210.2 | 2615-2715 |
| ITGAX | NM_000887.3 | 700-800 |
| ITK | NM_005546.3 | 3430-3530 |
| ITM2A | NM_004867.4 | 988-1088 |
| JAK3 | NM_000215.2 | 1715-1815 |
| JAKMIP1 | NM_001099433.1 | 1765-1865 |
| JUP | NM_002230.2 | 1075-1175 |
| KIF2C | NM_006845.3 | 1940-2040 |
| KIR2DL1 | NM_014218.2 | 1316-1416 |
| KIR2DL4 | NM_001080770.1 | 841-941 |
| KLK11 | NM_006853.2 | 886-986 |
| KLK5 | NM_001077491.1 | 830-930 |
| KLRB1 | NM_002258.2 | 85-185 |
| KLRC1 | NM_002259.3 | 335-435 |
| KLRC2 | NM_002260.3 | 942-1042 |
| KLRD1 | NM_002262.3 | 542-642 |
| KLRG1 | NM_005810.3 | 65-165 |
| KLRG2 | NM_198508.2 | 1347-1447 |
| KLRK1 | NM_007360.1 | 760-860 |
| KRAS | NM_004985.3 | 1790-1890 |
| KRT13 | NM_002274.3 | 1548-1648 |
| KRT17 | NM_000422.2 | 514-614 |
| KRT5 | NM_000424.2 | 130-230 |
| KRT6A | NM_005554.3 | 117-217 |
| KRT6B | NM_005555.3 | 2095-2195 |
| LAG3 | NM_002286.5 | 1735-1835 |
| LAIR1 | NM_002287.3 | 1195-1295 |
| LAMP1 | NM_005561.3 | 730-830 |
| LAMP2 | NM_002294.2 | 380-480 |
| LAT | NM_001014987.1 | 1290-1390 |

TABLE 4-continued

Set of 680 Normalization Genes

| Gene Id | Target Transcript NCBI Accession # | Exemplary Target Region |
|---|---|---|
| LAT2 | NM_014146.3 | 1863-1963 |
| LAX1 | NM_001136190.1 | 315-415 |
| LCK | NM_005356.2 | 1260-1360 |
| LGALS1 | NM_002305.3 | 60-160 |
| LGALS2 | NM_006498.2 | 314-414 |
| LGALS3 | NM_001177388.1 | 495-595 |
| LGALS3BP | NM_005567.3 | 1700-1800 |
| LGALS4 | NM_006149.3 | 995-1095 |
| LGALS7 | NM_002307.3 | 246-346 |
| LGALS9 | NM_002308.3 | 935-1035 |
| LIFR | NM_002310.3 | 2995-3095 |
| LILRA1 | NM_006863.1 | 1719-1819 |
| LILRA2 | NM_006866.2 | 317-417 |
| LILRA3 | NM_006865.3 | 1123-1223 |
| LILRA4 | NM_012276.3 | 1577-1677 |
| LILRA5 | NM_181879.2 | 545-645 |
| LILRA6 | NM_024318.2 | 1900-2000 |
| LILRB1 | NM_001081637.1 | 2332-2432 |
| LILRB2 | NM_005874.1 | 595-695 |
| LILRB3 | NM_006864.2 | 2235-2335 |
| LILRB4 | NM_001081438.1 | 1825-1925 |
| LILRB5 | NM_001081442.1 | 327-427 |
| LMO3 | NM_001001395.2 | 490-590 |
| LSR | NM_205835.3 | 1888-1988 |
| LST1 | NR_029461.1 | 164-264 |
| LTA | NM_000595.2 | 885-985 |
| LTB | NM_002341.1 | 330-430 |
| LTBR | NM_002342.1 | 1435-1535 |
| LTK | NM_002344.5 | 564-664 |
| LY6E | NM_002346.2 | 380-480 |
| LY6G6C | NM_025261.2 | 170-270 |
| LY6G6D | NM_021246.2 | 39-139 |
| LY9 | NM_001033667.1 | 260-360 |
| LYPD3 | NM_014400.2 | 1280-1380 |
| MAF | NM_005360.4 | 2198-2298 |
| MAFB | NM_005461.3 | 1655-1755 |
| MAGEA1 | NM_004988.4 | 476-576 |
| MAP4K1 | NM_007181.3 | 780-880 |
| MARCO | NM_006770.3 | 1434-1534 |
| MBL2 | NM_000242.2 | 1756-1856 |
| MDM2 | NM_006878.2 | 280-380 |
| MERTK | NM_006343.2 | 665-765 |
| MICA | NM_000247.1 | 550-650 |
| MICB | NM_005931.3 | 1387-1487 |
| MITF | NM_000248.3 | 3240-3340 |
| MKI67 | NM_002417.2 | 4020-4120 |
| MLANA | NM_005511.1 | 779-879 |
| MLH1 | NM_000249.2 | 1605-1705 |
| MMP11 | NM_005940.3 | 260-360 |
| MMP13 | NM_002427.2 | 951-1051 |
| MMP9 | NM_004994.2 | 1530-1630 |
| MN1 | NM_002430.2 | 1610-1710 |
| MON1B | NM_014940.2 | 2880-2980 |
| MRC1 | NM_002438.2 | 525-625 |
| MS4A1 | NM_152866.2 | 620-720 |
| MSH2 | NM_000251.1 | 2105-2205 |
| MSH4 | NM_002440.3 | 472-572 |
| MSLN | NM_013404.3 | 1178-1278 |
| MTA2 | NM_004739.3 | 615-715 |
| MUC21 | NM_001010909.2 | 2760-2860 |
| MX1 | NM_002462.2 | 1485-1585 |
| MYBL2 | NM_002466.2 | 445-545 |
| MYC | NM_002467.3 | 1610-1710 |
| MYH4 | NM_017533.2 | 3935-4035 |
| NAPSA | NM_004851.1 | 511-611 |
| NCAM1 | NM_000615.5 | 1620-1720 |
| NCR1 | NM_004829.5 | 602-702 |
| NCR2 | NM_004828.3 | 306-406 |
| NCR3 | NM_147130.1 | 50-150 |
| NCR3LG1 | NM_001202439.1 | 1294-1394 |
| NFATC1 | NM_172389.1 | 1984-2084 |
| NFIL3 | NM_005384.2 | 1795-1895 |
| NFKB1 | NM_003998.2 | 1675-1775 |
| NKG7 | NM_005601.3 | 632-732 |
| NKX2-1 | NM_003317.3 | 2011-2111 |
| NLRP10 | NM_176821.3 | 175-275 |
| NOD1 | NM_006092.1 | 3285-3385 |
| NOS2 | NM_000625.4 | 605-705 |
| NR4A2 | NM_006186.3 | 1380-1480 |
| NT5E | NM_002526.2 | 1214-1314 |
| OAS2 | NM_016817.2 | 480-580 |
| OAZ1 | NM_004152.2 | 313-413 |
| OSCAR | NM_130771.3 | 990-1090 |
| OVOL2 | NM_021220.2 | 676-776 |
| P2RY8 | NM_178129.3 | 425-525 |
| PARK7 | NM_001123377.1 | 254-354 |
| PBK | NM_018492.2 | 755-855 |
| PCSK1 | NM_000439.3 | 2273-2373 |
| PCSK2 | NM_002594.2 | 645-745 |
| PDCD1 | NM_005018.1 | 175-275 |
| PDCD1LG2 | NM_025239.3 | 235-335 |
| PDCD4 | NM_014456.3 | 1115-1215 |
| PDGFRA | NM_006206.3 | 1925-2025 |
| PECAM1 | NM_000442.3 | 1365-1465 |
| PF4 | NM_002619.3 | 109-209 |
| PGR | NM_000926.4 | 3246-3346 |
| PHACTR2 | NM_001100164.1 | 8350-8450 |
| PHLDA3 | NM_012396.3 | 532-632 |
| PI3 | NM_002638.3 | 274-374 |
| PIK3CA | NM_006218.2 | 2445-2545 |
| PIK3CB | NM_006219.1 | 2945-3045 |
| PIK3CD | NM_005026.3 | 95-195 |
| PIK3CG | NM_002649.2 | 2125-2225 |
| PIK3R1 | NM_181504.2 | 1105-1205 |
| PILRA | NM_178273.1 | 663-763 |
| PILRB | NM_178238.1 | 1165-1265 |
| PLA2G6 | NM_001004426.1 | 1954-2054 |
| PLAT | NM_000931.2 | 1334-1434 |
| PLSCR1 | NM_021105.2 | 355-455 |
| POLR1B | NM_019014.3 | 3320-3420 |
| POLR2A | NM_000937.3 | 3775-3875 |
| POSTN | NM_001135935.1 | 910-1010 |
| PPARG | NM_015869.3 | 1035-1135 |
| PPIA | NM_021130.2 | 925-1025 |
| PPP1R2 | NM_006241.4 | 146-246 |
| PPP1R9A | NM_017650.2 | 1060-1160 |
| PRC1 | NM_199414.1 | 1927-2027 |
| PRDM1 | NM_182907.1 | 310-410 |
| PRF1 | NM_005041.3 | 2120-2220 |
| PRKCB | NM_212535.1 | 1750-1850 |
| PROM2 | NM_001165977.1 | 1388-1488 |
| PRR15L | NM_024320.2 | 1005-1105 |
| PRSS8 | NM_002773.3 | 917-1017 |
| PSMB10 | NM_002801.2 | 221-321 |
| PSMB8 | NM_004159.4 | 1215-1315 |
| PSMB9 | NM_002800.4 | 455-555 |
| PSME1 | NM_006263.2 | 825-925 |
| PSME2 | NM_002818.2 | 315-415 |
| PSTPIP1 | NM_003978.3 | 1339-1439 |
| PSTPIP2 | NM_024430.3 | 885-985 |
| PTEN | NM_000314.3 | 1675-1775 |
| PTGER2 | NM_000956.2 | 1410-1510 |
| PTGER4 | NM_000958.2 | 1380-1480 |
| PTHLH | NM_198965.1 | 605-705 |
| PTPN13 | NM_080684.2 | 4890-4990 |
| PTPN22 | NM_015967.4 | 2505-2605 |
| PTPN3 | NM_001145372.1 | 2750-2850 |
| PTPN6 | NM_002831.5 | 1734-1834 |
| PTPN7 | NM_002832.3 | 2960-3060 |
| PTPRC | NM_080923.2 | 154-254 |
| PTPRCAP | NM_005608.2 | 668-768 |
| PTPRF | NM_002840.3 | 6310-6410 |
| PVR | NM_006505.3 | 604-704 |
| PVRIG | NM_024070.3 | 1390-1490 |
| PVRL2 | NM_002856.2 | 1337-1437 |
| PVRL3 | NM_015480.2 | 925-1025 |
| PYHIN1 | NM_198930.2 | 533-633 |
| RAB25 | NM_020387.2 | 245-345 |
| RAC2 | NM_002872.3 | 1069-1169 |
| RACGAP1 | NM_013277.3 | 1850-1950 |

TABLE 4-continued

Set of 680 Normalization Genes

| Gene Id | Target Transcript NCBI Accession # | Exemplary Target Region |
|---|---|---|
| RARRES2 | NM_002889.3 | 365-465 |
| RASAL3 | NM_022904.1 | 2161-2261 |
| RASSF8 | NM_007211.2 | 1235-1335 |
| RECK | NM_021111.2 | 2135-2235 |
| RETNLB | NM_032579.2 | 426-526 |
| RGN | NM_152869.2 | 1560-1660 |
| RGS16 | NM_002928.2 | 205-305 |
| RORA | NM_134261.2 | 1715-1815 |
| RORC | NM_001001523.1 | 1350-1450 |
| RPL19 | NM_000981.3 | 315-415 |
| RSAD2 | NM_080657.4 | 473-573 |
| RUNX1 | NM_001754.4 | 635-735 |
| RUNX3 | NM_004350.1 | 2085-2185 |
| S100A2 | NM_005978.3 | 567-667 |
| S100A8 | NM_002964.3 | 115-215 |
| S100A9 | NM_002965.2 | 75-175 |
| SAMD3 | NM_001017373.2 | 780-880 |
| SAMHD1 | NM_015474.2 | 640-740 |
| SART1 | NM_005146.3 | 3025-3125 |
| SART3 | NM_014706.3 | 1195-1295 |
| SASH3 | NM_018990.3 | 1815-1915 |
| SCGB2A2 | NM_002411.1 | 265-365 |
| SCUBE2 | NM_020974.1 | 1835-1935 |
| SDHA | NM_004168.1 | 230-330 |
| SELL | NR_029467.1 | 1585-1685 |
| SELPLG | NM_003006.3 | 2297-2397 |
| SEMA4A | NM_001193300.1 | 935-1035 |
| SEMA4D | NM_001142287.1 | 1120-1220 |
| SERPINA1 | NM_000295.4 | 760-860 |
| SERPINB5 | NM_002639.4 | 90-190 |
| SERPINF1 | NM_002615.4 | 888-988 |
| SFN | NM_006142.3 | 579-679 |
| SFTPA1B | NM_001093770.2 | 1885-1985 |
| SGPP2 | NM_152386.2 | 850-950 |
| SH2D1A | NM_002351.4 | 495-595 |
| SH2D1B | NM_053282.4 | 545-645 |
| SH2D2A | NM_001161443.1 | 341-441 |
| SIGLEC10 | NM_001171158.1 | 1425-1525 |
| SIGLEC14 | NM_001098612.1 | 1084-1184 |
| SIGLEC15 | NM_213602.2 | 124-224 |
| SIGLEC5 | NM_003830.2 | 2145-2245 |
| SIGLEC9 | NM_001198558.1 | 1052-1152 |
| SIRPA | NM_080792.2 | 3115-3215 |
| SIRPB1 | NM_006065.2 | 2130-2230 |
| SIRPG | NM_001039508.1 | 830-930 |
| SIT1 | NM_014450.2 | 720-820 |
| SLA | NM_001045556.2 | 980-1080 |
| SLA2 | NM_032214.2 | 1640-1740 |
| SLAMF1 | NM_003037.2 | 580-680 |
| SLAMF6 | NM_001184714.1 | 1032-1132 |
| SLAMF7 | NM_021181.3 | 215-315 |
| SLC2A1 | NM_006516.2 | 2500-2600 |
| SOCS3 | NM_003955.3 | 1870-1970 |
| SPN | NM_003123.3 | 2345-2445 |
| SRPX | NM_006307.2 | 1330-1430 |
| STARD10 | NM_006645.2 | 105-205 |
| STAT1 | NM_007315.2 | 205-305 |
| STAT6 | NM_003153.3 | 2030-2130 |
| STK11IP | NM_052902.2 | 565-665 |
| SYK | NM_003177.3 | 1685-1785 |
| SYP | NM_003179.2 | 2265-2365 |
| TAGAP | NM_054114.3 | 169-269 |
| TARP | NM_001003799.1 | 560-660 |
| TBC1D10B | NM_015527.3 | 2915-3015 |
| TBP | NM_001172085.1 | 587-687 |
| TBX21 | NM_013351.1 | 890-990 |
| TCN2 | NM_000355.2 | 1010-1110 |
| TEK | NM_000459.2 | 615-715 |
| TERT | NM_198253.1 | 2570-2670 |
| TF | NM_001063.2 | 640-740 |
| TGFB1 | NM_000660.3 | 1260-1360 |
| TGFBR2 | NM_001024847.1 | 1760-1860 |
| THEMIS | NM_001010923.2 | 1700-1800 |
| THY1 | NM_006288.2 | 135-235 |
| TIGIT | NM_173799.2 | 1968-2068 |
| TIMP3 | NM_000362.4 | 1640-1740 |
| TIMP4 | NM_003256.2 | 1000-1100 |
| TMC6 | NM_001127198.1 | 1870-1970 |
| TMEM2 | NM_013390.2 | 1120-1220 |
| TMEM246 | NM_032342.1 | 1108-1208 |
| TMIGD2 | NM_144615.2 | 359-459 |
| TNF | NM_000594.2 | 1010-1110 |
| TNFAIP3 | NM_006290.2 | 260-360 |
| TNFAIP6 | NM_007115.2 | 250-350 |
| TNFAIP8L2 | NM_024575.3 | 709-809 |
| TNFRSF10B | NM_003842.3 | 565-665 |
| TNFRSF11A | NM_003839.2 | 490-590 |
| TNFRSF13B | NM_012452.2 | 160-260 |
| TNFRSF13C | NM_052945.3 | 789-889 |
| TNFRSF14 | NM_003820.2 | 916-1016 |
| TNFRSF15 | NM_001204344.1 | 2338-2438 |
| TNFRSF17 | NM_001192.2 | 635-735 |
| TNFRSF18 | NM_004195.2 | 445-545 |
| TNFRSF21 | NM_014452.3 | 735-835 |
| TNFRSF25 | NM_001039664.1 | 158-258 |
| TNFRSF4 | NM_003327.2 | 200-300 |
| TNFRSF8 | NM_152942.2 | 2030-2130 |
| TNFRSF9 | NM_001561.4 | 255-355 |
| TNFSF10 | NM_003810.2 | 115-215 |
| TNFSF11 | NM_003701.2 | 490-590 |
| TNFSF13A | NM_003808.3 | 810-910 |
| TNFSF13B | NM_006573.4 | 1430-1530 |
| TNFSF14 | NM_003807.2 | 270-370 |
| TNFSF18 | NM_005092.2 | 175-275 |
| TNFSF4 | NM_003326.2 | 545-645 |
| TNFSF8 | NM_001244.3 | 518-618 |
| TNFSF9 | NM_003811.3 | 398-498 |
| TOX | NM_014729.2 | 574-674 |
| TOX3 | NM_001080430.1 | 1925-2025 |
| TP63 | NM_001114978.1 | 1175-1275 |
| TRAT1 | NM_016388.2 | 770-870 |
| TREM1 | NM_018643.3 | 375-475 |
| TREM2 | NM_018965.2 | 563-663 |
| TREML1 | NM_178174.2 | 775-875 |
| TREML2 | NM_024807.2 | 2745-2845 |
| TREML4 | NM_198153.2 | 1715-1815 |
| TRIM16 | NM_006470.3 | 84-184 |
| TRIM29 | NM_012101.3 | 2645-2745 |
| TSLP | NM_033035.4 | 899-999 |
| TSPAN32 | NM_005705.4 | 828-928 |
| TUBB | NM_178014.2 | 320-420 |
| TYR | NM_000372.4 | 1195-1295 |
| TYRO3 | NM_006293.2 | 775-875 |
| TYROBP | NM_003332.3 | 361-461 |
| UBASH3A | NM_001001895.1 | 1970-2070 |
| UBASH3B | NM_032873.4 | 2494-2594 |
| UBB | NM_018955.2 | 795-895 |
| UBE2C | NM_181803.1 | 269-369 |
| VCAM1 | NM_001078.3 | 2535-2635 |
| VEGFA | NM_001025366.1 | 1325-1425 |
| VIM | NM_003380.2 | 694-794 |
| VTCN1 | NM_024626.2 | 1375-1475 |
| WT1 | NM_000378.3 | 2160-2260 |
| XIST | NR_001564.1 | 1020-1120 |
| ZAP70 | NM_001079.3 | 1175-1275 |
| ZBTB16 | NM_006006.4 | 1585-1685 |
| ZBTB32 | NM_014383.1 | 1620-1720 |
| ZBTB34 | NM_001099270.1 | 406-506 |
| ZEB1 | NM_001128128.1 | 1450-1550 |
| ZEB2 | NM_001171653.1 | 240-340 |
| ZKSCAN5 | NM_014569.3 | 3688-3788 |

Each of the steps of obtaining a blood sample, isolating total RNA therefrom for a gene signature biomarker assay, performing the assay, and determining gene signature scores may be performed by separate individuals/entities at separate locations. For example, a nurse may obtain a blood sample from a cancer patient and then send the blood sample to a laboratory, which may process the blood sample to isolate and prepare total RNA for the assay. The total RNA may be assayed soon after preparation, or stored for future assay. The lab that prepared the total RNA may conduct the assay or send the prepared RNA to a different lab to conduct the assay. The gene signature score may be calculated by a trained professional who is employed by the lab or is an independent contractor. Alternatively, a single diagnostic lab obtains the blood sample from the subject's physician and then performs all of the steps involved in preparing total RNA, assaying the RNA and calculating the gene signature score for the blood sample.

In some embodiments, the individuals involved with isolating total RNA from a blood sample assaying the RNA for a gene signature biomarker do not know the identity of the patient whose sample is being tested; i.e., the sample received by the laboratory is made anonymous in some manner before being sent to the laboratory. For example, the sample may be merely identified by a number or some other code (a "sample ID") and the results of the assay are reported to the party ordering the test using the sample ID. In preferred embodiments, the link between the identity of a patient and the patient's tissue sample is known only to the patient or to the patient's physician.

In some embodiments, after the test results have been obtained, the diagnostic laboratory generates a test report, which may comprise any or both of the following information: (1) the blood sample was biomarker positive or negative and (2) the gene signature score for the patient's blood sample and the reference score for that gene signature. The test report may also include a list of genes whose expression was analyzed in the assay.

In other embodiments, the test report may also include guidance on how to interpret the results for predicting if a patient is likely to respond to a PD-1 antagonist.

In some embodiments, the test report is a written document prepared by the diagnostic laboratory and sent to the patient or the patient's physician as a hard copy or via electronic mail. In other embodiments, the test report is generated by a computer program and displayed on a video monitor in the physician's office. The test report may also comprise an oral transmission of the test results directly to the patient or the patient's physician or an authorized employee in the physician's office. Similarly, the test report may comprise a record of the test results that the physician makes in the patient's file.

Detecting the presence or absence of a blood-based gene signature of the invention may be performed using a kit that has been specially designed for this purpose. In one embodiment, the kit comprises a set of oligonucleotide probes capable of hybridizing to the target transcripts in the gene signature. The kit may further comprise oligonucleotide probes capable of detecting transcripts of other genes, such as control genes, or genes used for normalization purposes. he set of oligonucleotide probes may comprise an ordered array of oligonucleotides on a solid surface, such as a microchip, silica beads (such as BeadArray technology from Illumina, San Diego, Calif.), or a glass slide (see, e.g., WO 98/20020 and WO 98/20019). In some embodiments, the oligonucleotide probes are provided in one or more compositions in liquid or dried form.

Oligonucleotides in kits of the invention must be capable of specifically hybridizing to a target region of a polynucleotide, such as for example, an RNA transcript or cDNA generated therefrom. As used herein, specific hybridization means the oligonucleotide forms an anti-parallel double-stranded structure with the target region under certain hybridizing conditions, while failing to form such a structure with non-target regions when incubated with the polynucleotide under the same hybridizing conditions. The composition and length of each oligonucleotide in the kit will depend on the nature of the transcript containing the target region as well as the type of assay to be performed with the oligonucleotide and is readily determined by the skilled artisan.

In some embodiments, each oligonucleotide in the kit is a perfect complement of its target region. An oligonucleotide is said to be a "perfect" or "complete" complement of another nucleic acid molecule if every nucleotide of one of the molecules is complementary to the nucleotide at the corresponding position of the other molecule. While perfectly complementary oligonucleotides are preferred for detecting transcripts in a gene signature, departures from complete complementarity are contemplated where such departures do not prevent the molecule from specifically hybridizing to the target region as defined above. For example, an oligonucleotide probe may have one or more non-complementary nucleotides at its 5' end or 3' end, with the remainder of the probe being completely complementary to the target region. Alternatively, non-complementary nucleotides may be interspersed into the probe as long as the resulting probe is still capable of specifically hybridizing to the target region.

In some preferred embodiments, each oligonucleotide in the kit specifically hybridizes to its target region under stringent hybridization conditions. Stringent hybridization conditions are sequence-dependent and vary depending on the circumstances. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. As the target sequences are generally present in excess, at Tm, 50% of the probes are occupied at equilibrium.

Typically, stringent conditions include a salt concentration of at least about 0.01 to 1.0 M sodium ion concentration (or other salts) at pH 7.0 to 8.3 and the temperature is at least about 25° C. for short oligonucleotide probes (e.g., 10 to 50 nucleotides). Stringent conditions can also be achieved with the addition of destabilizing agents such as formamide. For example, conditions of 5×SSPE (750 mM NaCl, 50 mM NaPhosphate, 5 mM EDTA, pH 7.4) and a temperature of 25-30° C. are suitable for allele-specific probe hybridizations. Additional stringent conditions can be found in Molecular Cloning: A Laboratory Manual, Sambrook et al., Cold Spring Harbor Press, Cold Spring Harbor, N.Y. (1989), chapters 7, 9, and 11, and in NUCLEIC ACID HYBRIDIZATION, A PRACTICAL APPROACH, Haymes et al., IRL Press, Washington, D.C., 1985.

One non-limiting example of stringent hybridization conditions includes hybridization in 4× sodium chloride/sodium citrate (SSC), at about 65-70° C. (or alternatively hybridization in 4×SSC plus 50% formamide at about 42-50° C.) followed by one or more washes in 1×SSC, at about 65-70° C. A non-limiting example of highly stringent hybridization conditions includes hybridization in 1×SSC, at about 65-70° C. (or alternatively hybridization in 1×SSC plus 50% formamide at about 42-50° C.) followed by one or more washes in 0.3×SSC, at about 65-70° C. A non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Stringency conditions with ranges intermediate to the above-recited values, e.g., at 65-70° C. or at 42-50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete.

The hybridization temperature for hybrids anticipated to be less than 50 base pairs in length should be 5-10° C. less than the melting temperature ($T_m$) of the hybrid, where Tm is determined according to the following equations. For hybrids less than 18 base pairs in length, $T_m$ (° C.)=2(# of A+T bases)+4(# of G+C bases). For hybrids between 18 and 49 base pairs in length, $T_m$ (° C.)=81.5+16.6($\log_{10}$[Na+])+ 0.41(% G+C)−(600/N), where N is the number of bases in the hybrid, and [Na+] is the concentration of sodium ions in the hybridization buffer ([Na+] for 1×SSC=0.165 M).

The oligonucleotides in kits of the invention may be comprised of any phosphorylation state of ribonucleotides, deoxyribonucleotides, and acyclic nucleotide derivatives, and other functionally equivalent derivatives. Alternatively, the oligonucleotides may have a phosphate-free backbone, which may be comprised of linkages such as carboxymethyl, acetamidate, carbamate, polyamide (peptide nucleic acid (PNA)) and the like (Varma, in MOLECULAR BIOLOGY AND BIOTEChNOLOGY, A COMPREHENSIVE DESK REFERENCE, Meyers, ed., pp. 6 17-20, VCH Publishers, Inc., 1995). The oligonucleotides may be prepared by chemical synthesis using any suitable methodology known in the art, or may be derived from a biological sample, for example, by restriction digestion. The oligonucleotides may contain a detectable label, according to any technique known in the art, including use of radiolabels, fluorescent labels, enzymatic labels, proteins, haptens, antibodies, sequence tags and the like. The oligonucleotides in the kit may be manufactured and marketed as analyte specific reagents (ASRs) or may be constitute components of an approved diagnostic device.

Kits of the invention may also contain other reagents such as hybridization buffer and reagents to detect when hybridization with a specific target molecule has occurred. Detection reagents may include biotin-or fluorescent-tagged oligonucleotides and/or an enzyme-labeled antibody and one or more substrates that generate a detectable signal when acted on by the enzyme. It will be understood by the skilled artisan that the set of oligonucleotides and reagents for performing the assay will be provided in separate receptacles placed in the kit container if appropriate to preserve biological or chemical activity and enable proper use in the assay.

In other embodiments, each of the oligonucleotide probes and all other reagents in the kit have been quality tested for optimal performance in an assay designed to determine the signature score of a gene signature of interest in a blood sample. In some embodiments, the kit includes an instruction manual that describes how to use the determined gene signature score to assign, to the tested blood sample, the presence or absence of a gene signature biomarker that predicts response to treatment with a PD-1 antagonist.

B. Pharmaceutical Compositions, Drug Products and Treatment Regimens

An individual to be treated by any of the methods and products described herein is a human subject diagnosed with a tumor, and appropriate baseline and post-dose blood samples are available or obtainable to use in testing for the presence or absence of any of the gene signature biomarkers described herein.

The blood sample can be collected from a subject before and/or after exposure of the subject to one or more therapeutic treatment regimens, such as for example, a PD-1 antagonist, a chemotherapeutic agent, radiation therapy. Accordingly, blood samples may be collected from a subject over a period of time.

A physician may use a patient's score for a gene signature of the invention as a guide in deciding how to treat a patient who has been diagnosed with a type of cancer that is susceptible to treatment with a PD-1 antagonist or other chemotherapeutic agent(s). For example, prior to initiation of treatment with the PD-1 antagonist or the other chemotherapeutic agent(s), the physician would typically order a diagnostic test to determine if a baseline blood sample collected from the patient is positive or negative for an OxPhos gene signature biomarker and/or to obtain baseline signature scores for a PD-L1 gene signature or an IFNG gene signature. The physician could then order a subsequent blood draw after the patient is treated with a first dose of the PD-1 antagonist to use in obtaining a post-dose signature score for a PD-L1 or IFNG gene signature and thus assign to the patient the presence or absence of the predictive biomarker. In some embodiments, a physician may be considering whether to treat the patient with a pharmaceutical product that is indicated for patients who tests positive for the gene signature biomarker. For example, if the patient tests positive for the biomarker, the patient is treated with a therapeutic regimen that includes at least the PD-1 antagonist (optionally in combination with one or more chemotherapeutic agents), and if the patient test negative for the biomarker, the patient is treated with a therapeutic regimen that does not include any PD-1 antagonist.

In deciding how to use gene signature test results in treating any individual patient, the physician may also take into account other relevant circumstances, such as the stage of the cancer, weight, gender, and general condition of the patient, including inputting a combination of these factors and the gene signature biomarker test results into a model that helps guide the physician in choosing a therapy and/or treatment regimen with that therapy.

The physician may choose to treat the patient who tests biomarker positive with a combination therapy regimen that includes a PD-1 antagonist and one or more additional therapeutic agents. The additional therapeutic agent may be, e.g., a chemotherapeutic, a biotherapeutic agent (including but not limited to antibodies to VEGF, EGFR, Her2/neu, VEGF receptors, other growth factor receptors, CD20, CD40, CD-40L, CTLA-4, OX-40, 4-1BB, and ICOS), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF).

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin;

duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gamma1I and calicheamicin phiI1, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2, 2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

Each therapeutic agent in a combination therapy used to treat a biomarker positive patient may be administered either alone or in a medicament (also referred to herein as a pharmaceutical composition) which comprises the therapeutic agent and one or more pharmaceutically acceptable carriers, excipients and diluents, according to standard pharmaceutical practice.

Each therapeutic agent in a combination therapy used to treat a biomarker positive patient may be administered simultaneously (i.e., in the same medicament), concurrently (i.e., in separate medicaments administered one right after the other in any order) or sequentially in any order. Sequential administration is particularly useful when the therapeutic agents in the combination therapy are in different dosage forms (one agent is a tablet or capsule and another agent is a sterile liquid) and/or are administered on different dosing schedules, e.g., a chemotherapeutic that is administered at least daily and a biotherapeutic that is administered less frequently, such as once weekly, once every two weeks, or once every three weeks.

In some embodiments, at least one of the therapeutic agents in the combination therapy is administered using the same dosage regimen (dose, frequency and duration of treatment) that is typically employed when the agent is used as monotherapy for treating the same cancer. In other embodiments, the patient receives a lower total amount of at least one of the therapeutic agents in the combination therapy than when the agent is used as monotherapy, e.g., smaller doses, less frequent doses, and/or shorter treatment duration.

Each therapeutic agent in a combination therapy used to treat a biomarker positive patient can be administered orally or parenterally, including the intravenous, intramuscular, intraperitoneal, subcutaneous, rectal, topical, and transdermal routes of administration.

A patient may be administered a PD-1 antagonist prior to or following surgery to remove a tumor and may be used prior to, during or after radiation therapy.

In some embodiments, a PD-1 antagonist is administered to a patient who has not been previously treated with a biotherapeutic or chemotherapeutic agent, i.e., is treatment-naïve. In other embodiments, the PD-1 antagonist is administered to a patient who failed to achieve a sustained response after prior therapy with a biotherapeutic or chemotherapeutic agent, i.e., is treatment-experienced.

A therapy comprising a PD-1 antagonist is typically used to treat a tumor that is large enough to be found by palpation or by imaging techniques well known in the art, such as MM, ultrasound, or CAT scan. In some preferred embodiments, the therapy is used to treat an advanced stage tumor having dimensions of at least about 200 mm$^3$, 300 mm$^3$, 400 mm$^3$, 500 mm$^3$, 750 mm$^3$, or up to 1000 mm$^3$.

Selecting a dosage regimen (also referred to herein as an administration regimen) for a therapy comprising a PD-1 antagonist depends on several factors, including the serum or tissue turnover rate of the entity, the level of symptoms, the immunogenicity of the entity, and the accessibility of the target cells, tissue or organ in the individual being treated. Preferably, a dosage regimen maximizes the amount of the PD-1 antagonist that is delivered to the patient consistent with an acceptable level of side effects. Accordingly, the dose amount and dosing frequency depends in part on the particular PD-1 antagonist, any other therapeutic agents to be used, and the severity of the cancer being treated, and patient characteristics. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602; Physicians' Desk Reference 2003 (Physicians' Desk Reference, 57th Ed); Medical Economics Company; ISBN: 1563634457; 57th edition (November 2002). Determination of the appropriate dosage regimen may be made by the clinician, e.g., using parameters or factors known or suspected in the art to affect treatment or predicted to affect treatment, and will depend, for example, the patient's clinical history (e.g., previous therapy), the type and stage of the cancer to be treated and biomarkers of response to one or more of the therapeutic agents in the combination therapy.

Biotherapeutic agents used in combination with a PD-1 antagonist may be administered by continuous infusion, or by doses at intervals of, e.g., daily, every other day, three times per week, or one time each week, two weeks, three weeks, monthly, bimonthly, etc. A total weekly dose is generally at least 0.05 μg/kg, 0.2 μg/kg, 0.5 μg/kg, 1 μg/kg, 10 μg/kg, 100 μg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J. Med.* 349:427-434; Herold et al. (2002) *New Engl. J. Med.* 346:1692-1698; Liu et al. (1999) *J. Neurol. Neurosurg. Psych.* 67:451-456; Portielji et al. (20003) *Cancer Immunol. Immunother.* 52:133-144.

In some embodiments that employ an anti-human PD-1 mAb as the PD-1 antagonist, the dosing regimen will comprise administering the anti-human PD-1 mAb at a dose of 1, 2, 3, 5 or 10 mg/kg at intervals of about 14 days (±2 days) or about 21 days (±2 days) or about 30 days (±2 days) throughout the course of treatment.

In other embodiments that employ an anti-human PD-1 mAb as the PD-1 antagonist, the dosing regimen will comprise administering the anti-human PD-1 mAb at a dose of from about 0.005 mg/kg to about 10 mg/kg, with intra-patient dose escalation. In other escalating dose embodiments, the interval between doses will be progressively shortened, e.g., about 30 days (±2 days) between the first and second dose, about 14 days (±2 days) between the second and third doses. In certain embodiments, the dosing interval will be about 14 days (±2 days), for doses subsequent to the second dose.

In certain embodiments, a subject will be administered an intravenous (IV) infusion of a medicament comprising any of the PD-1 antagonists described herein, and such administration may be part of a treatment regimen employing the PD-1 antagonist as a monotherapy regimen or as part of a combination therapy.

In one preferred embodiment of the invention, the PD-1 antagonist is nivolumab, which is administered intravenously at a dose selected from the group consisting of: 1 mg/kg Q2W, 2 mg/kg Q2W, 3 mg/kg Q2W, 5 mg/kg Q2W, 10 mg Q2W, 1 mg/kg Q3W, 2 mg/kg Q3W, 3 mg/kg Q3W, 5 mg/kg Q3W, and 10 mg Q3W.

In another preferred embodiment of the invention, the PD-1 antagonist is pembrolizumab, which is administered in a liquid medicament at a dose selected from the group consisting of 200 mg Q3W, 1 mg/kg Q2W, 2 mg/kg Q2W, 3 mg/kg Q2W, 5 mg/kg Q2W, 10 mg Q2W, 1 mg/kg Q3W, 2 mg/kg Q3W, 3 mg/kg Q3W, 5 mg/kg Q3W, and 10 mg/kg Q3W or equivalents of any of these doses (e.g., a PK model for pembrolizumab estimates that the fixed dose of 200 mg Q3W provides exposures that are consistent with those obtained with 2 mg/kg Q3Q). In some particularly preferred embodiments, pembrolizumab is administered as a liquid medicament which comprises 25 mg/ml pembrolizumab, 7% (w/v) sucrose, 0.02% (w/v) polysorbate 80 in 10 mM histidine buffer pH 5.5, and the selected dose of the medicament is administered by IV infusion over a time period of 30 minutes. The optimal dose for pembrolizumab in combination with any other therapeutic agent may be identified by dose escalation.

The present invention also provides a medicament which comprises a PD-1 antagonist as described above and a pharmaceutically acceptable excipient. When the PD-1 antagonist is a biotherapeutic agent, e.g., a mAb, the antagonist may be produced in CHO cells using conventional cell culture and recovery/purification technologies.

In some embodiments, a medicament comprising an anti-PD-1 antibody as the PD-1 antagonist may be provided as a liquid formulation or prepared by reconstituting a lyophilized powder with sterile water for injection prior to use. WO 2012/135408 describes the preparation of liquid and lyophilized medicaments comprising pembrolizumab that are suitable for use in the present invention. In some preferred embodiments, a medicament comprising pembrolizumab is provided in a glass vial which contains about 50 mg of pembrolizumab.

Exemplary Specific Embodiments of the Invention

1. A method for testing a patient for the presence or absence of an on-treatment biomarker that predicts that the patient is likely to have an anti-tumor response to treatment with a PD-1 antagonist, which comprises:
   (a) obtaining a sample of total intracellular RNA that has been isolated from a baseline blood sample collected from the patient,
   (b) measuring the baseline raw RNA expression level in the isolated RNA for each gene in a gene signature,
   (c) normalizing the measured baseline raw RNA expression levels
   (d) calculating a baseline signature score for the gene signature from the normalized RNA expression levels,
   (e) obtaining a sample of total intracellular RNA that has been isolated from a post-dose blood sample collected from the patient,
   (f) measuring the post-dose raw RNA expression level in the isolated RNA for each gene in the gene signature,
   (g) normalizing each of the measured post-dose raw RNA expression levels;
   (h) calculating a post-dose signature score for the gene signature from the normalized RNA expression levels
   (i) calculating a post-dose signature score for the gene signature from the measured RNA expression levels, and
   (j) comparing the post-dose score to the baseline score, and (k) classifying the patient as biomarker positive or biomarker negative; wherein the patient is classified as biomarker positive if the post-dose signature score is greater than the baseline signature score the patient and the patient is classified as biomarker negative if the post-dose signature score is equal to or less than the baseline signature score, wherein steps b-d may be performed before, concurrently with, or after steps f-h, and wherein the gene signature comprises a set of genes selected from the group consisting of:
  (1) PD-L1, PD-L2, LAG3, STAT1, and CXCL10;
  (2) PD-L1, PD-L2, LAG3, STAT1, CXCL10 and CLEC10a;
  (3) CXCL9, CXCL10, HLA-DRA, IDOL and STAT1;
  (4) CXCL9, CXCL10, HLA-DRA, IDOL IFNG, and STAT1;
  (5) CCR5, CXCL9, CXCL10, CXCL11, GZMA, HLA-DRA, IDO1, IFNG, PRF1 and STAT1; and
  (6) CCR5, CLEC10a, CXCL9, CXCL10, CXCL11, GZMA, HLA-DRA, IDO1, IFNG, LAG3, PD-L1, PD-L2, PRF1, and STAT1.

2. The method of embodiment 1, wherein calculating the baseline signature score comprises determining the arithmetic mean of the normalized baseline RNA expression levels for each of the genes in the signature and calculating the post-dose signature score comprises determining the arithmetic mean of the normalized post-dose RNA expression levels for each of the genes in the signature.

3. The method of embodiment 1 or 2, wherein the post-dose blood sample was collected after administration of a single dose of the PD-1 antagonist to the patient.

4. The method of embodiment 3, wherein the post-dose blood sample was collected between about two weeks and about four weeks after administration of the single dose of the PD-1 antagonist.

5. A method for testing a patient for the presence or absence of a baseline biomarker that predicts that the patient is likely to have an anti-tumor response to treatment with a PD-1 antagonist, which comprises:
  (a) obtaining a sample of total intracellular RNA that has been isolated from a baseline blood sample collected from the patient,
  (b) measuring the baseline raw RNA expression level in the isolated RNA for each gene in a gene signature which comprises (a) each of ATP5G2, ATP5G3, ATP5J2, COX7C, NDUFA12, NDUFA13, NDUFA3, NDUFA7, NDUFB11, NDUFB4, and NDUFS5 or (b) a subset of said genes,
  (c) normalizing the measured baseline raw RNA expression levels,
  (d) calculating a baseline signature score for the gene signature from the normalized RNA expression levels, and
  (e) comparing the baseline signature score to a reference score for the gene signature, and
  (f) classifying the patient as biomarker positive or biomarker negative; wherein the patient is classified as biomarker positive if the baseline signature score is equal to or lower than the reference score and the patient is classified as biomarker negative if the baseline signature score is greater than the reference signature score.

6. The method of embodiment 5, wherein calculating the baseline signature score comprises determining the arithmetic mean of the normalized baseline RNA expression levels for each of the genes in the signature.

7. A method of treating a patient diagnosed with a tumor which comprises:
  (a) collecting a baseline blood sample from the patient,
  (b) administering at least one dose of a PD-1 antagonist to the patient,
  (c) collecting a post-dose blood sample from the patient,
  (d) obtaining a signature score for a gene signature biomarker in each of the baseline and post-dose blood samples, and
  (e) treating the patient with a therapeutic regimen that comprises a PD-1 antagonist if the post-dose signature score is greater than the baseline signature score or treating the subject with a therapeutic regimen that does not include a PD-1 antagonist if the post-dose score is equal to or less than the baseline score;

wherein the gene signature comprises a set of genes selected from the group consisting of:
  (1) PD-L1, PD-L2, LAG3, STAT1, and CXCL10;
  (2) PD-L1, PD-L2, LAG3, STAT1, CXCL10 and CLEC10a;
  (3) CXCL9, CXCL10, HLA-DRA, IDOL and STAT1;
  (4) CXCL9, CXCL10, HLA-DRA, IDOL IFNG, and STAT1;
  (5) CCR5, CXCL9, CXCL10, CXCL11, GZMA, HLA-DRA, IDOL IFNG, PRF1 and STAT1; and
  (6) CCR5, CLEC10a, CXCL9, CXCL10, CXCL11, GZMA, HLA-DRA, IDOL IFNG, LAG3, PD-L1, PD-L2, PRF1, and STAT1.

8. A method of treating a patient diagnosed with a tumor which comprises:
  (a) determining if a baseline blood sample collected from the patient is positive or negative for a gene signature biomarker which predicts that the patient is likely to have an anti-tumor response to a PD-1 antagonist, and
  (b) treating the patient with a therapeutic regimen that comprises a PD-1 antagonist if the biomarker is present or treating the subject with a therapeutic regimen that does not include a PD-1 antagonist if the biomarker is absent, wherein the biomarker comprises 6 to 11 of the following genes: ATP5G2, ATP5G3, ATP5J2, COX7C, NDUFA12, NDUFA13, NDUFA3, NDUFA7, NDUFB11, NDUFB4, and NDUFS5.

9 The method of embodiment 8, wherein the determining step comprises:
  obtaining the baseline blood sample from the patient;
  sending the blood sample to a laboratory with a request to test the sample for the presence or absence of the biomarker; and
  receiving a report from the laboratory that states whether the tumor sample is biomarker positive or biomarker negative.

10. A pharmaceutical composition for use in treating cancer in a patient who tests positive for a blood-based biomarker, wherein the composition comprises a PD-1 antagonist and at least one pharmaceutically acceptable excipient, and wherein
the blood-based biomarker is an on-treatment biomarker which comprises a gene signature selected from the group consisting of:
  (1) PD-L1, PD-L2, LAG3, STAT1, and CXCL10;
  (2) PD-L1, PD-L2, LAG3, STAT1, CXCL10 and CLEC10a;
  (3) CXCL9, CXCL10, HLA-DRA, IDOL and STAT1;
  (4) CXCL9, CXCL10, HLA-DRA, IDOL IFNG, and STAT1;

(5) CCR5, CXCL9, CXCL10, CXCL11, GZMA, HLA-DRA, IDOL IFNG, PRF1 and STAT1; and
(6) CCR5, CLEC10a, CXCL9, CXCL10, CXCL11, GZMA, HLA-DRA, IDOL IFNG, LAG3, PD-L1, PD-L2, PRF1, and STAT1, or the blood-based biomarker is a baseline biomarker which comprises a gene signature that is comprised of 6 to 11 of the following genes: ATP5G2, ATP5G3, ATP5J2, COX7C, NDUFA12, NDUFA13, NDUFA3, NDUFA7, NDUFB11, NDUFB4, and NDUFS5.

11. A drug product which comprises a pharmaceutical composition and prescribing information, wherein the pharmaceutical composition comprises a PD-1 antagonist and at least one pharmaceutically acceptable excipient and the prescribing information states that the pharmaceutical composition is indicated for use in treating cancer in patients who have a blood test that is positive for a baseline biomarker or an on-treatment biomarker, wherein the baseline biomarker comprises a gene signature of 6 to 11 of the following genes: ATP5G2, ATP5G3, ATP5J2, COX7C, NDUFA12, NDUFA13, NDUFA3, NDUFA7, NDUFB11, NDUFB4, and NDUFS5 and the on-treatment biomarker comprises a gene signature selected from the group consisting of:
(1) PD-L1, PD-L2, LAG3, STAT1, and CXCL10;
(2) PD-L1, PD-L2, LAG3, STAT1, CXCL10 and CLEC10a;
(3) CXCL9, CXCL10, HLA-DRA, IDOL and STAT1;
(4) CXCL9, CXCL10, HLA-DRA, IDOL IFNG, and STAT1;
(5) CCR5, CXCL9, CXCL10, CXCL11, GZMA, HLA-DRA, IDOL IFNG, PRF1 and STAT1; and
(6) CCR5, CLEC10a, CXCL9, CXCL10, CXCL11, GZMA, HLA-DRA, IDOL IFNG, LAG3, PD-L1, PD-L2, PRF1, and STAT1.

12. A kit for assaying a blood sample to determine a score for a biomarker that predicts anti-tumor response to a PD-1 antagonist, wherein the kit comprises a first set of hybridization probes for detecting expression of each gene in a gene signature, wherein the gene signature is selected from the group consisting of:
(1) PD-L1, PD-L2, LAG3, STAT1, and CXCL10;
(2) PD-L1, PD-L2, LAG3, STAT1, CXCL10 and CLEC10a;
(3) CXCL9, CXCL10, HLA-DRA, IDOL and STAT1;
(4) CXCL9, CXCL10, HLA-DRA, IDOL IFNG, and STAT1;
(5) CCR5, CXCL9, CXCL10, CXCL11, GZMA, HLA-DRA, IDOL IFNG, PRF1 and STAT1;
(6) CCR5, CLEC10a, CXCL9, CXCL10, CXCL11, GZMA, HLA-DRA, IDOL IFNG, LAG3, PD-L1, PD-L2, PRF1, and STAT1; and
(7) 6 to 11 of the following genes: ATP5G2, ATP5G3, ATP5J2, COX7C, NDUFA12, NDUFA13, NDUFA3, NDUFA7, NDUFB11, NDUFB4, and NDUFS5.

13. The kit of embodiment 12, which further comprises a second set of hybridization probes for detecting expression of each gene in a set of normalization genes.

14. The method of any of embodiments 1 to 6, wherein the measuring step comprises contacting the isolated RNA molecules with at least one hybridization probe for the transcript listed in Table 4 for each gene whose expression is to be measured, wherein the contacting is performed under stringent hybridization conditions, and quantitating the number of probe-RNA hybrids generated in the contacting step.

15. The method of any of embodiments 1 to 6, wherein the measuring step comprises amplifying and quantifying the transcript listed in Table 4 for each gene whose expression is to be measured.

14. The method of any of embodiments 1 to 6 and 14 to 15, wherein the normalizing step comprises performing quantile normalization of raw RNA expression values relative to the distribution of raw RNA expression values in the patient blood sample and a plurality of control samples for a set of normalization genes, followed by a subsequent log 10-transformation.

15. The method of embodiment 14, wherein the normalization gene set consists essentially of at least 100, 200, 300, 400, 500, or 600 genes in Table 4.

16. The method, composition, drug product or kit of any of the above embodiments, wherein the on-treatment gene signature biomarker is selected from the group consisting of:
(a) PD-L1, PD-L2, LAG3, STAT1, CXCL10 and CLEC10a; and
(b) CCR5, CXCL9, CXCL10, CXCL11, GZMA, HLA-DRA, IDOL IFNG, PRF1 and STAT1.

17. The method, composition, drug product or kit of any of the above embodiments, wherein the anti-tumor response is against melanoma or Hodgkin's Lymphoma.

18. The method, composition, drug product or kit of any of the above embodiments, wherein the PD-1 antagonist is a monoclonal antibody, or an antigen binding fragment thereof, which specifically binds to PD-1 or to PD-L1 and blocks the binding of PD-L1 to PD-1.

24. The method, composition, drug product or kit of any of the above embodiments, wherein the PD-1 antagonist is nivolumab, pembrolizumab, a pembrolizumab biosimilar or a pembrolizumab variant.

25. The method, composition, drug product or kit of any of the above embodiments, wherein the anti-tumor response is clinical benefit, a partial response or a complete response.

EXAMPLES

Example 1. Collection of Whole Blood Samples and Subsequent Gene Expression Analysis Using the NanoString nCounter™System or the Illumina TrueSeq NGS System 1. Patient Cohort:

Keynote-001 is a phase 1 study sponsored by Merck Sharp and Dohme Corp. to assess the safety and efficacy of single-agent pembrolizumab in patients with progressive locally advanced or metastatic carcinoma, melanoma and NSCLC. A secondary objective of Keynote-001 is to investigate the correlation between biomarkers and the anti-tumor activity of pembrolizumab. Exploratory biomarker research included the collection of whole blood samples for gene expression profiling. Gene expression analysis was performed on baseline and post-dose blood samples for 44 melanoma patients from the Keynote-001 study. This cohort of 44 patients had the following characteristics.

75% of the patients had received previous ipilimumab treatment. Pembrolizumab dose & treatment schedules varied among the patients as follows:
10 mg/kg given once every 3 weeks (Q3W) (n=21)
10 mg/kg Q2W (n=12)
2 mg/kg Q3W (n=11)

The objective response rate (ORR) for pembrolizumab monotherapy in this cohort was 32% assessed per RECIST v1.1 by independent central review.

2. Blood Samples and RNA Preparation

Blood samples were collected and stabilized in PAXgene® Blood RNA Tubes PreAnalytiX® GmbH (Hombrechtikon, Switzerland). The baseline sample was collected on day 1 of the first treatment cycle (before administration of the first dose) and the post-dose sample was collected on the first day of the second treatment cycle (before administration of the second dose).

For gene expression analysis on the nCounter® Analysis System marketed by NanoString® Technologies, RNA was isolated and purified from the collected blood samples using the PAXgene® Blood RNA Kit RUO following the manufacturer's PAXgene Blood RNA procedure.

For gene expression analysis on the Illumina HiSeq 2000 and 2500 systems, RNA was isolated from the PAXgene Blood RNA Tubes and then sequenced on an Illumina gene sequencer according to manufacturer's instructions. In some experiments, the isolated RNA was further processed to remove globin mRNA and cytoplasmic and mitochondrial ribosomal RNA, using Illumina's TruSeq Stranded Total RNA with Ribo-Zero Globin kit. In earlier experiments which did not use that kit, additional filtering steps were applied to the sequencing data to remove artifacts caused be the presence of residual globin.

3. NanoString Gene Expression Analysis

Total RNA (50 ng-100 ng) isolated from blood samples that had been obtained from patients prior to or after one pembrolizumab dose were assayed for expression of the 680 gene set in Table 4 above using the NanoString nCounter® Analysis System and a CodeSet designed by NanoString to measure expression of the gene set in a single multiplex reaction for each sample. The CodeSet included the target transcript listed in Table 4 and a pair of capture and reporter probes for that transcript for each of the 680 genes. Hybridized samples were run on the NanoString nCounter™ preparation station using the manufacturer's high sensitivity protocol where excess capture and reporter probes were removed and transcript-specific ternary complexes were immobilized on a streptavidin-coated cartridge. The samples were scanned at maximum scan resolution capabilities using the nCounter™ Digital Analyzer.

For each patient sample, the raw transcript expression counts data were normalized by performing quantile normalization relative to the reference distribution and subsequent log 10-transformation. The reference distribution was generated by pooling reported counts for all samples after excluding values for technical (both positive and negative control) probes, and without performing intermediate normalization relying on negative (background-adjusted) or positive (synthetic sequences spiked with known titrations.

4. RNA Seq Gene Expression Analysis

Fragments Per Kilobase of exon per Million fragments mapped (FPKM) values were transformed using log 10(0.01+FPKM) and subsequently normalized by the upper quartile measured over approximately 20,000 transcripts corresponding to protein-coding genes. This transformation generates values that are close to log 10 for large input values and close to linear scale for low values (<1). Genes with maximum count below 10 were deemed not reliably detected and so were filtered out. In the earlier experiments, normalized data was de-trended twice: first by adjusting out the first principal component (found to be highly correlated with the expression of globin-related genes: HBA1, HBA2, and HBB), and then also adjusting out the second principal component (found to be highly correlated to HEMGN and defining a distinct set of ten samples that were not treated with the same globin-clear kit as the rest of the samples). In the later experiment (RNA processed with TruSeq Stranded Total RNA with Ribo-Zero Globin kit), no significant correlation between the first principal components and above genes was observed and therefore no additional de-trending steps were deemed necessary. Principal component analysis did not identify any profiles as likely outliers based on the gene expression data. Covariance between blood modules (Chausabel & Pulendran) was observed to be consistent across several blood data sets (as reflected in an evaluation of the melanoma cohort of 44 patient samples, 324 additional melanoma blood samples, and 264 NSCLC blood samples.

5. Gene Signature Scoring

Scores for each gene signature of interest was generated by taking the arithmetic mean of normalized expression for each gene in the signature.

Example 2. Analysis of PD-L1 and IFNG Gene Signature Scores and Anti-Tumor Response in Melanoma Patients Treated with Pembrolizumab Formal hypothesis testing was applied to associating gene signature scores with clinical outcomes as the inventors remained blinded to the clinical outcome data prior to finalization of the statistical analysis plan and construction of gene signature scores.

PD-1 and PD-L1 RNA expression measured by RNA-Seq was analyzed by paired t-test comparing baseline and post-dose levels in blood samples across the 44 melanoma patients and the results shown in FIG. 1. The X-axis shoes −log(10p) values of 1, 2, 3, 4, which correspond to p-values of 0.1, 0.01, 0.001, and 0.0001 respectively. The first dotted vertical line corresponds to a p-value 0.05. The Y-axis shows estimates of false discovery rate by Benjamini Hochberg method. Statistically significant post-single dose changes in expression of PD-1 and PD-L1 were observed, with p-values p-value<0.001 and p-value<0.01, respectively. However, the individual gene expression post-dose changes for PD-1 and PD-L1 did not show a significant association with ORR.

Figure 2A:
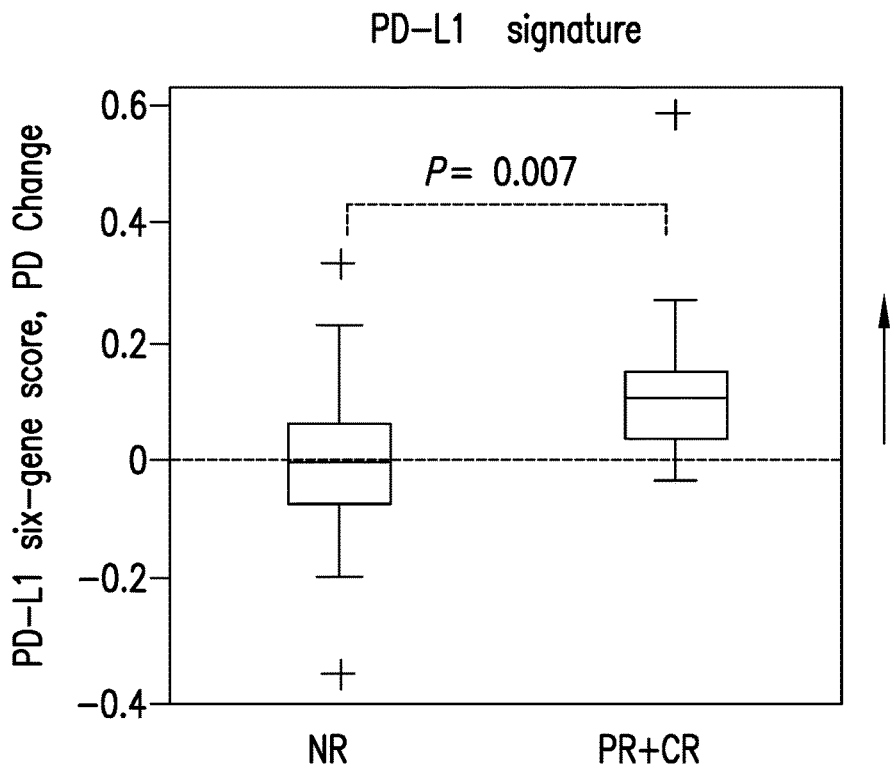
FIGS. 2A and 2B are boxplots showing the post-single dose (PD) change in scores for exemplary PD-L1 (FIG. 2A) and IFNG (FIG. 2B) gene signatures assayed in RNA isolated from blood samples collected from 43 patients in the MEL Cohort (y-axis) plotted against response determinations for the cohort that were made after continued treatment with pembrolizumab, with patients who had stable disease or progressive disease grouped as nonresponders (NR) and patients who had a partial response grouped with patients who had a complete response (PR+CR).
Figure 2B:
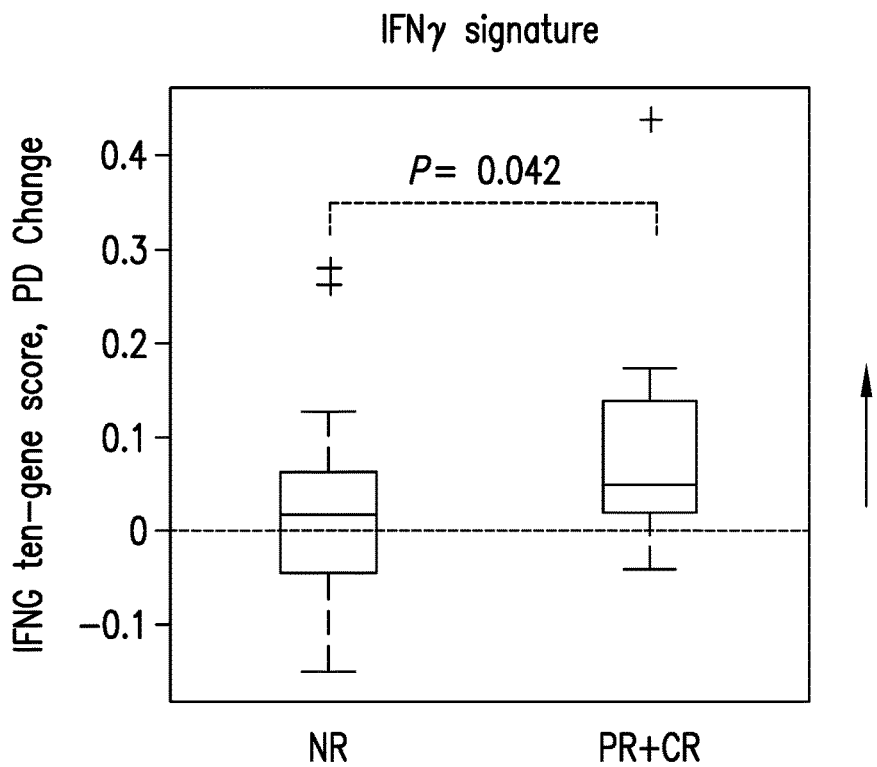
Figure 3A:
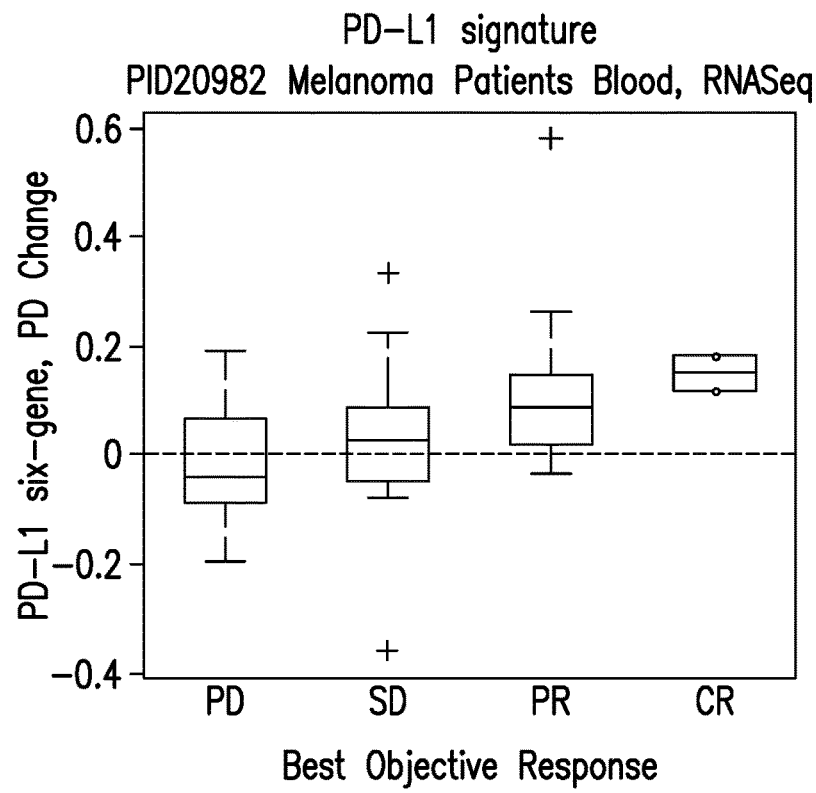
FIGS. 3A and 3B are boxplots showing the post-single dose (PD) changes in the scores for the same gene signatures and patients as in FIGS. 2A and 2B and the patients classified by response classifications of progressive disease (PD), stable disease (SD), partial response (PR) or complete response (CR).
Figure 3B:
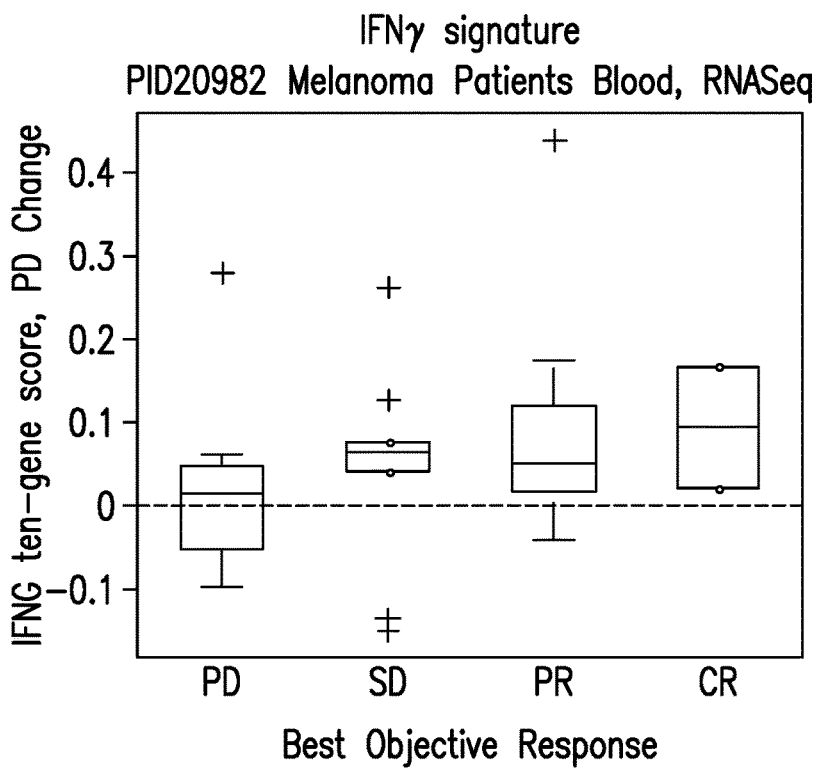

The inventors also examined post-dose expression changes for a 6-gene PD-L1 signature and a 10-gene IFNG signature which had been found to be predictive of anti-tumor response when measured in baseline tumor samples. Post-dose increases in the blood for both the IFNG and PD-L1 signatures measured using NanoString were found to be positively associated with clinical response (ORR) to pembrolizumab therapy: IFNG P-value=0.042 (FDR=0.174) and PD-L1 P-value=0.007 (FDR=0.144) (See FIG. 2). Similar results were obtained when the same signatures were scored using RNA measured with RNA-Seq (compare FIGS. 2 and 3).

Figure 4A:
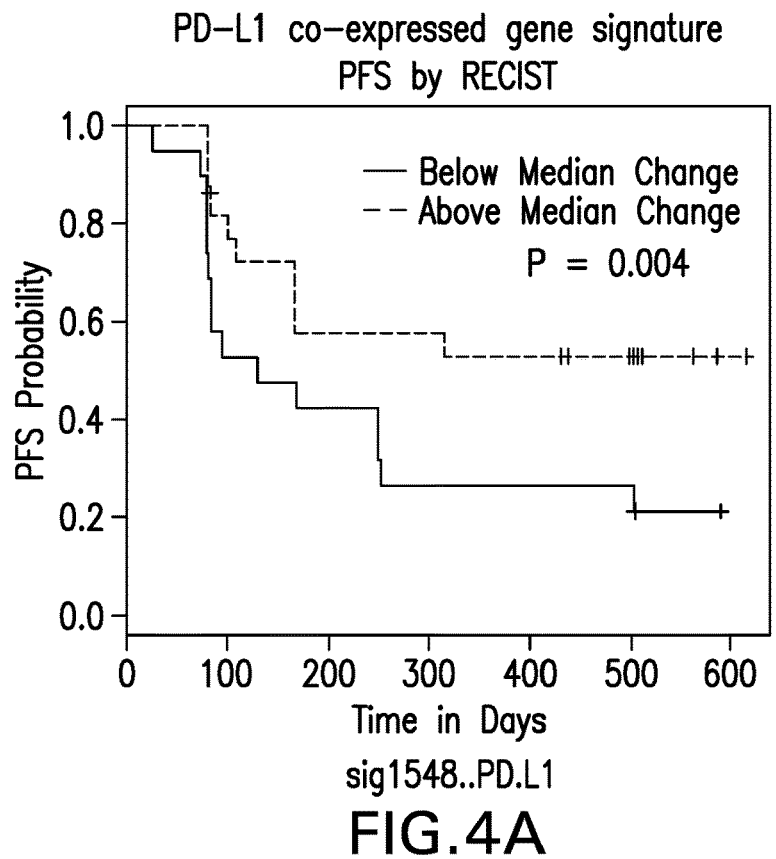
FIGS. 4A and 4B illustrate survival outcomes for subsets of the MEL cohort with a post-dose change in the score for an exemplary PD-L1 gene signature that was either above (dashed line) or below (solid line) the median post-dose change for the entire cohort, with FIG. 4A showing length of progression free survival (PFS) and FIG. 4B showing length of overall survival (OS).
Figure 4B:
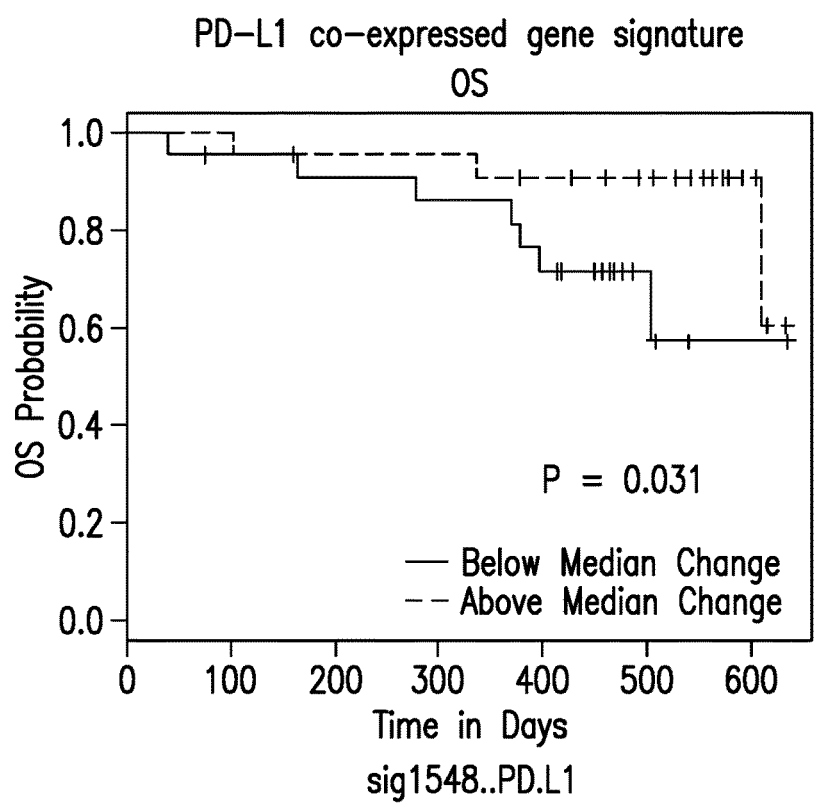
Figure 5A:
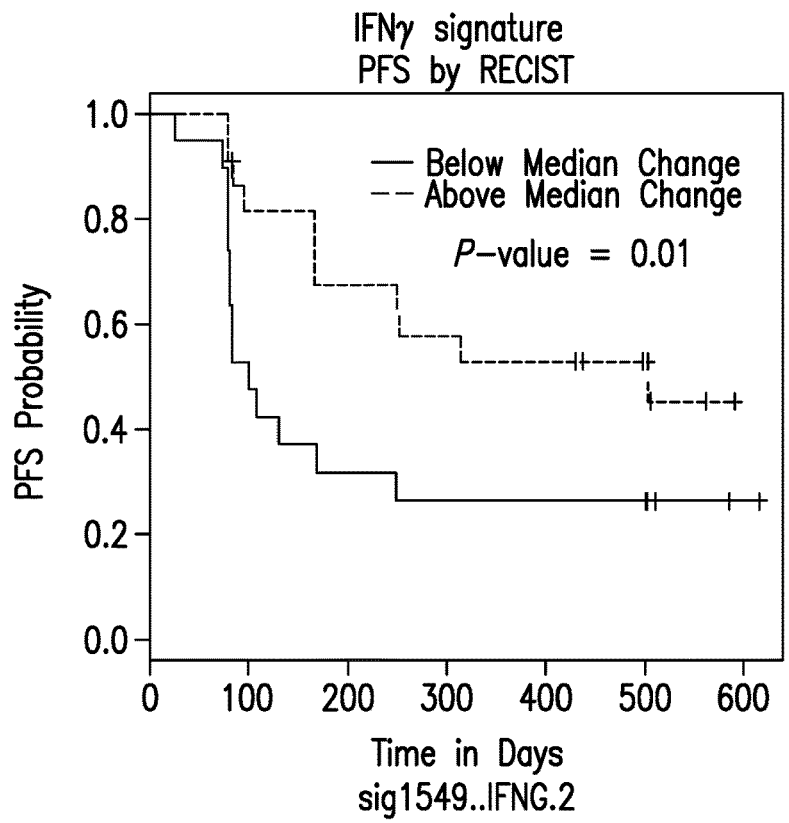
FIGS. 5A and 5B illustrate survival outcomes for subsets of the MEL cohort as in FIG. 1 who had a post-dose change in the score for an exemplary IFNG gene signature that was either above (dashed line) or below (solid line) the median post-dose change for the cohort, with FIG. 5A showing length of progression free survival (PFS) and FIG. 5B showing length of overall survival (OS).
Figure 5B:
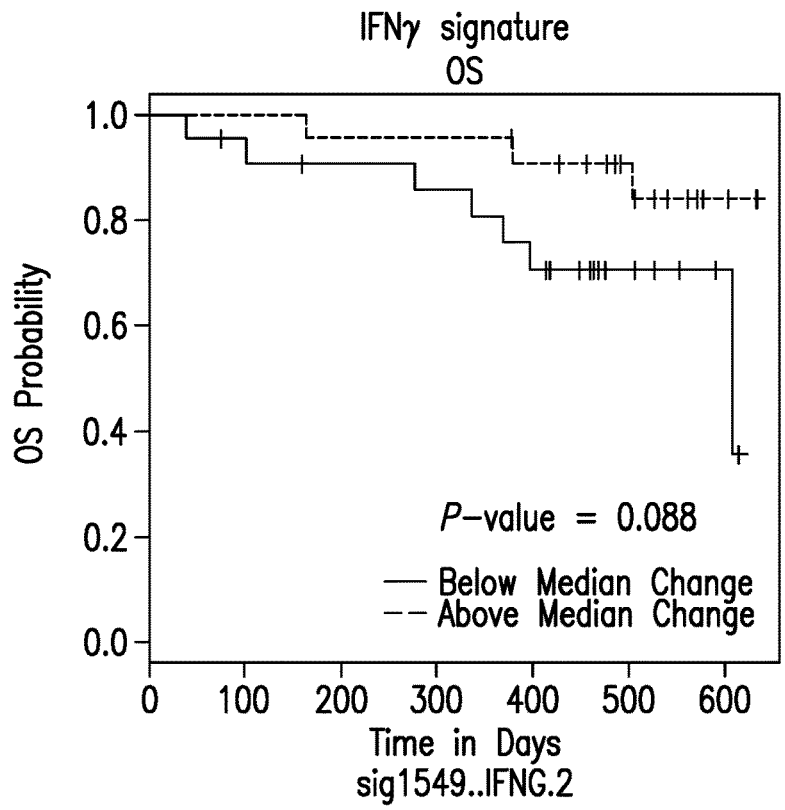

Post-dose changes for both signatures were also found to be associated with improved progression-free survival (PFS): IFNG P-value=0.010 (FDR=0.067) and PD-L1 P-value=0.004 (FDR=0.067) (see FIGS. 4 and 5).

Figure 6:
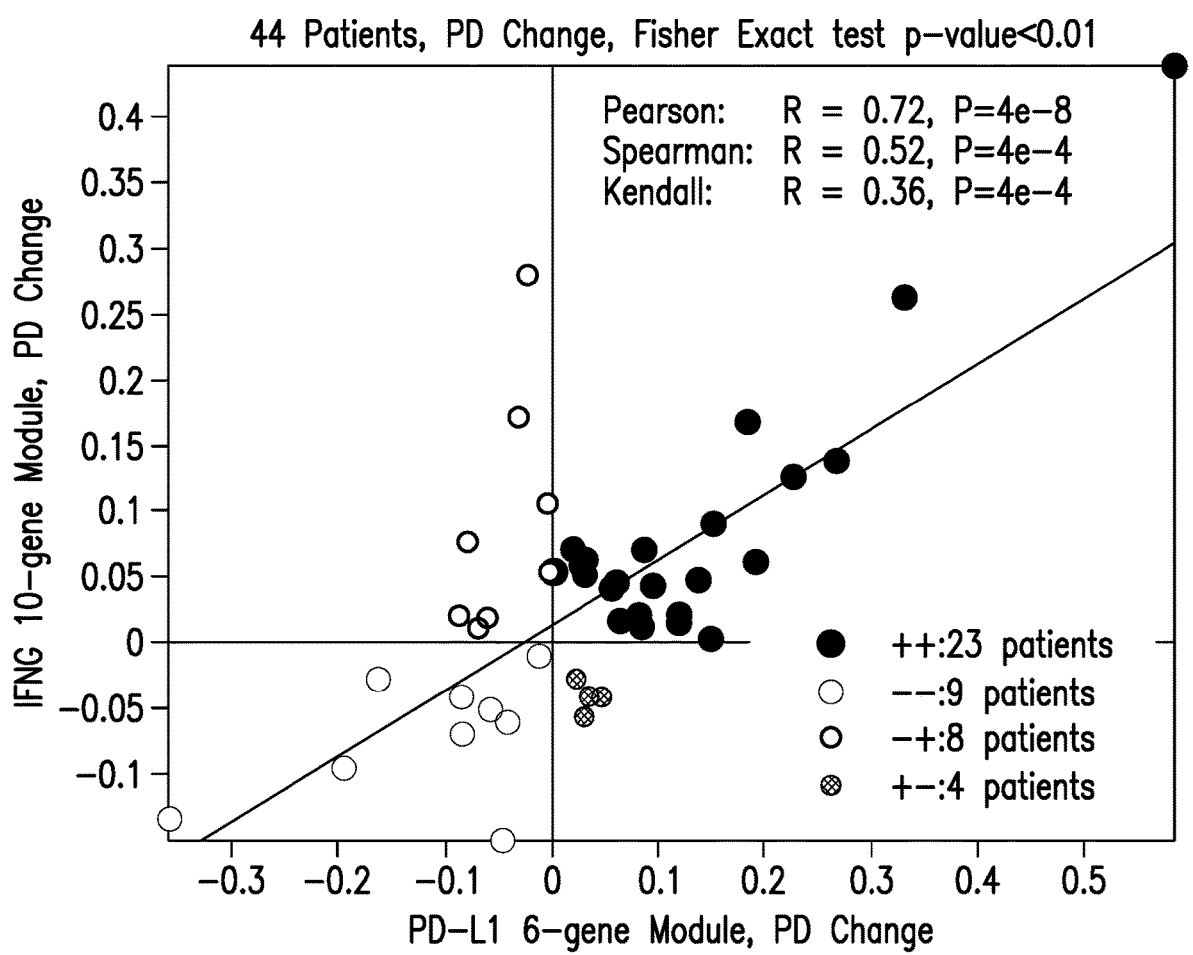
FIG. 6 illustrates the correlation between post-dose (PD) changes in patient scores determined using RNA sequencing for exemplary IFNG and PD-L1 gene signatures in baseline and post-dose blood samples obtained from the MEL Cohort.
Figure 7A:
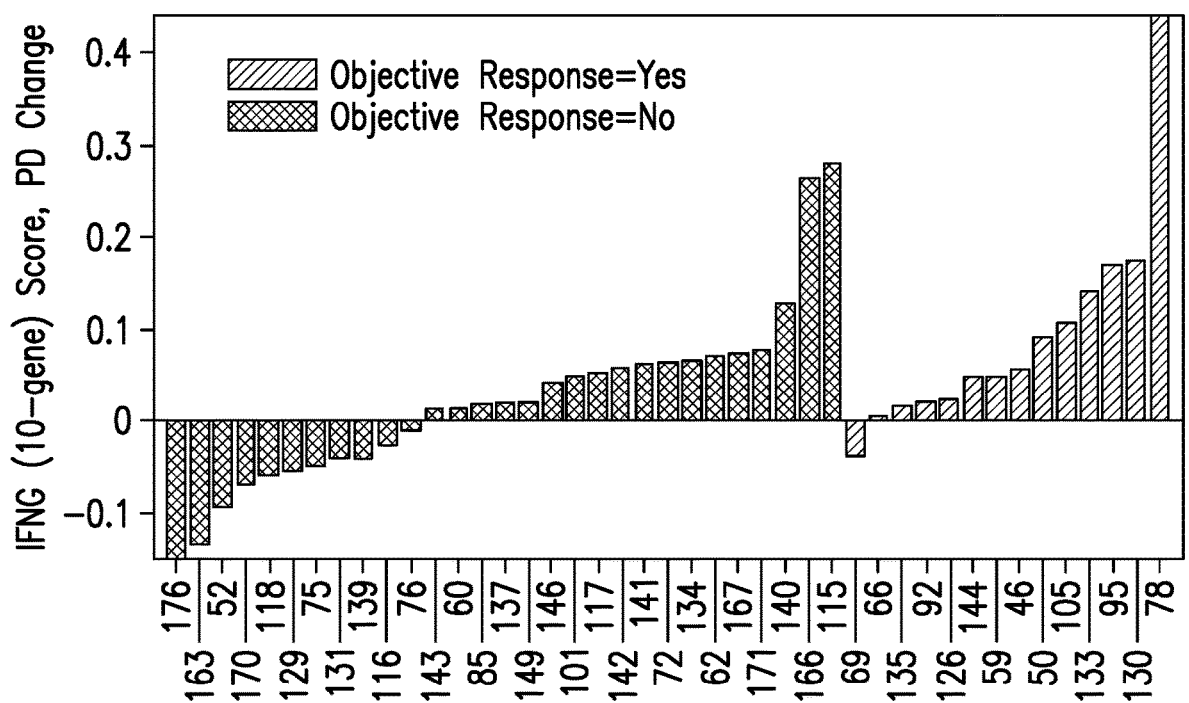
FIGS. 7A, 7B and 7C are waterfall plots showing post-dose changes in signature scores for exemplary on-treatment gene signatures determined for blood samples (Y-axis) from 43 individual patients in the MEL Cohort (X-axis) who had an objective response (PR or CR) (BOR=1) or did not have an objective response (BOR=0) to pembrolizumab therapy, with data for the IFNG 10-gene signature (FIG. 7A), the PD-L1 6-gene signature (FIG. 7B) and a 14 gene signature comprised of the unique genes in the IFNG and PD-L1 signatures FIG. 7C.
Figure 7B:
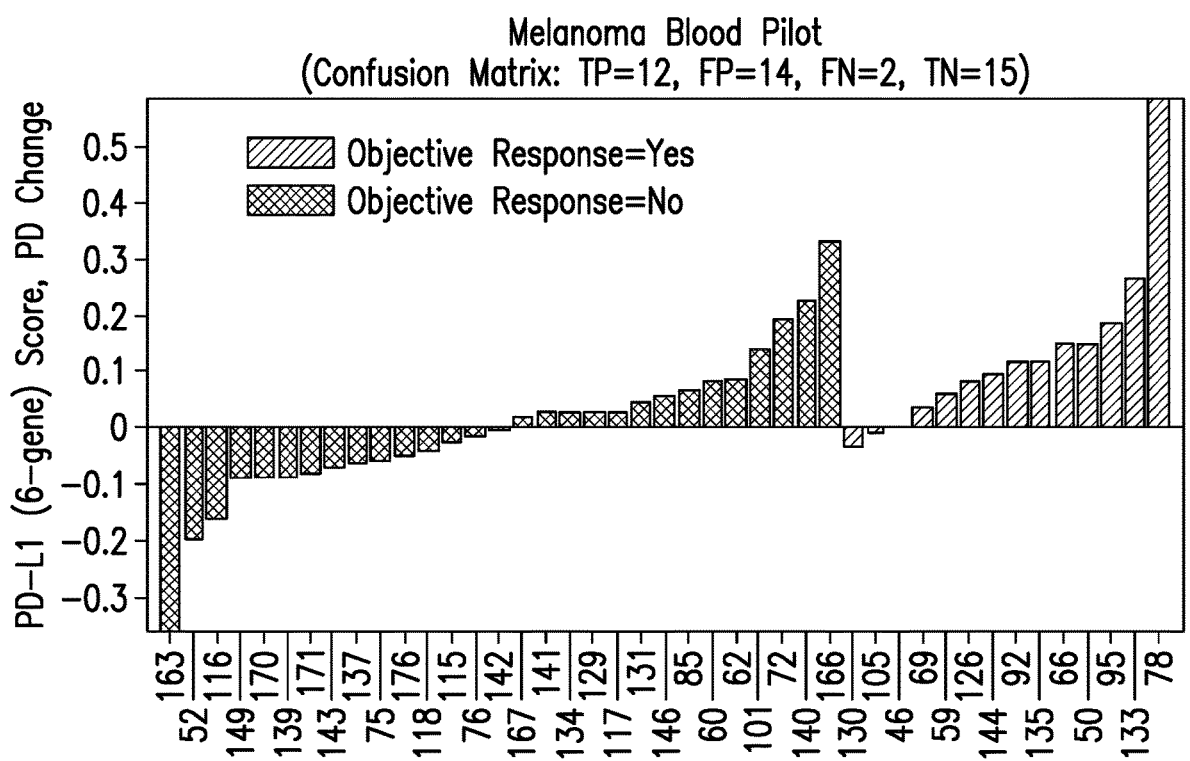
Figure 7C:
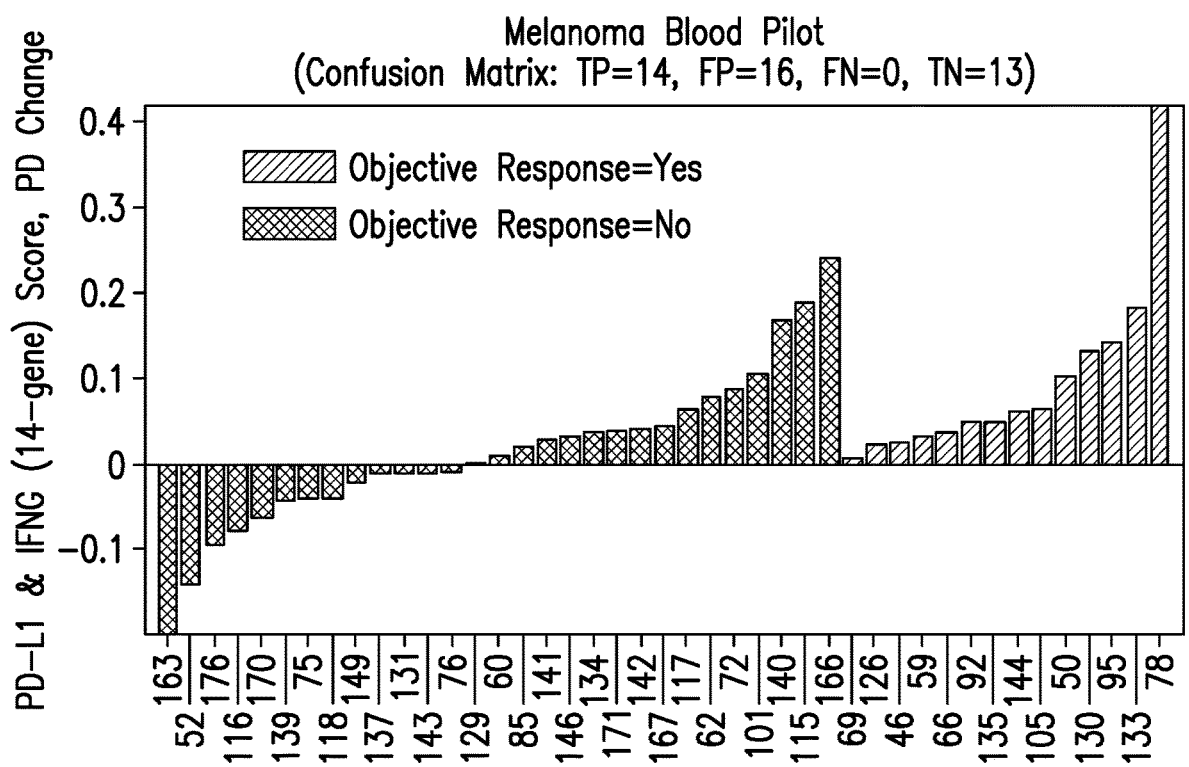
Figure 8A:
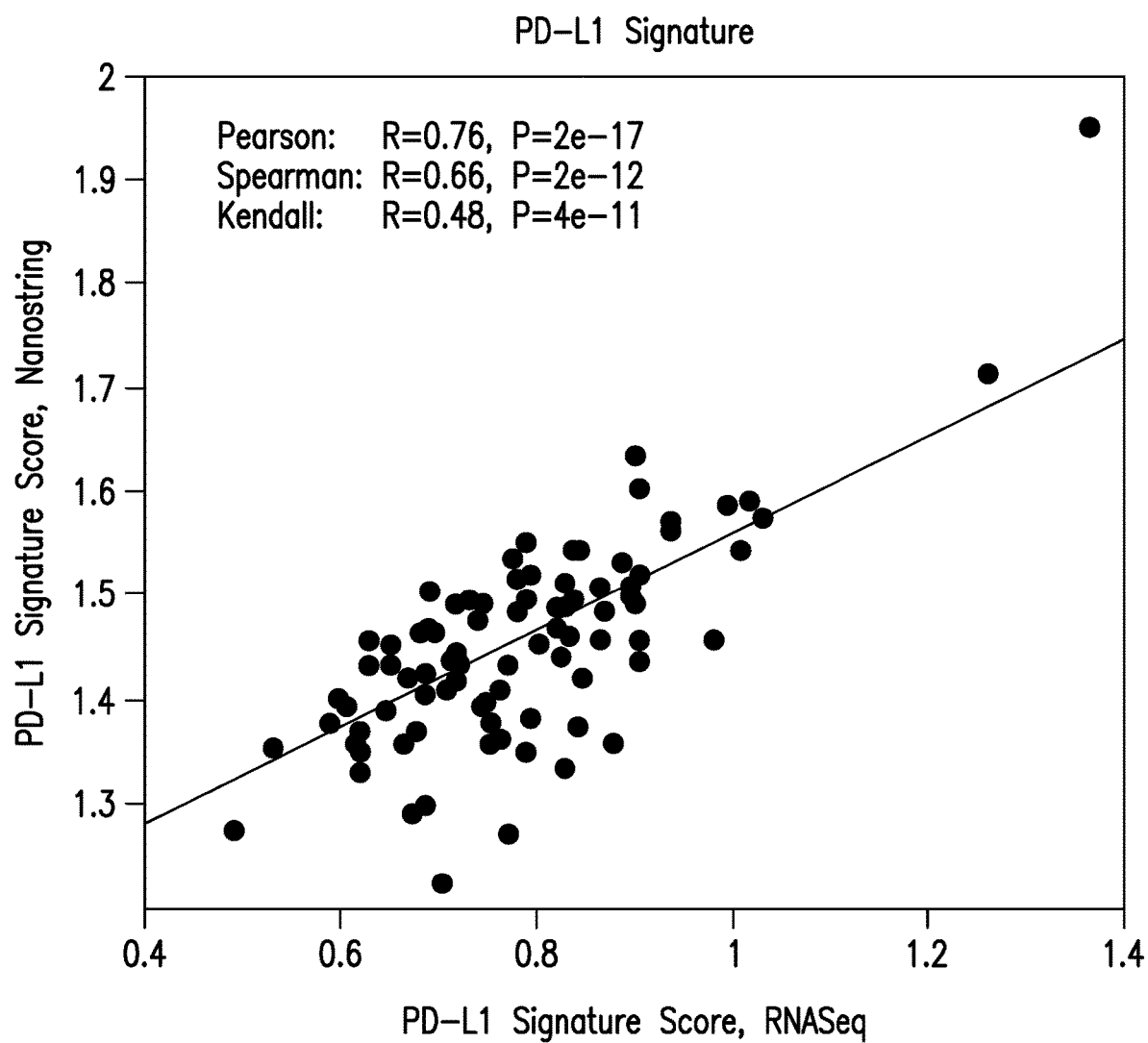
FIG. 8 illustrates the concordance between scores in the MEL Cohort for an exemplary PD-L1 gene signature (FIG. 8A) and an exemplary IFNG gene signature (FIG. 8B) that were determined with RNA expression values measured using the NanoString® platform (y-axis) or the Illumina® RNA-Seq platform (x-axis).
Figure 8B:
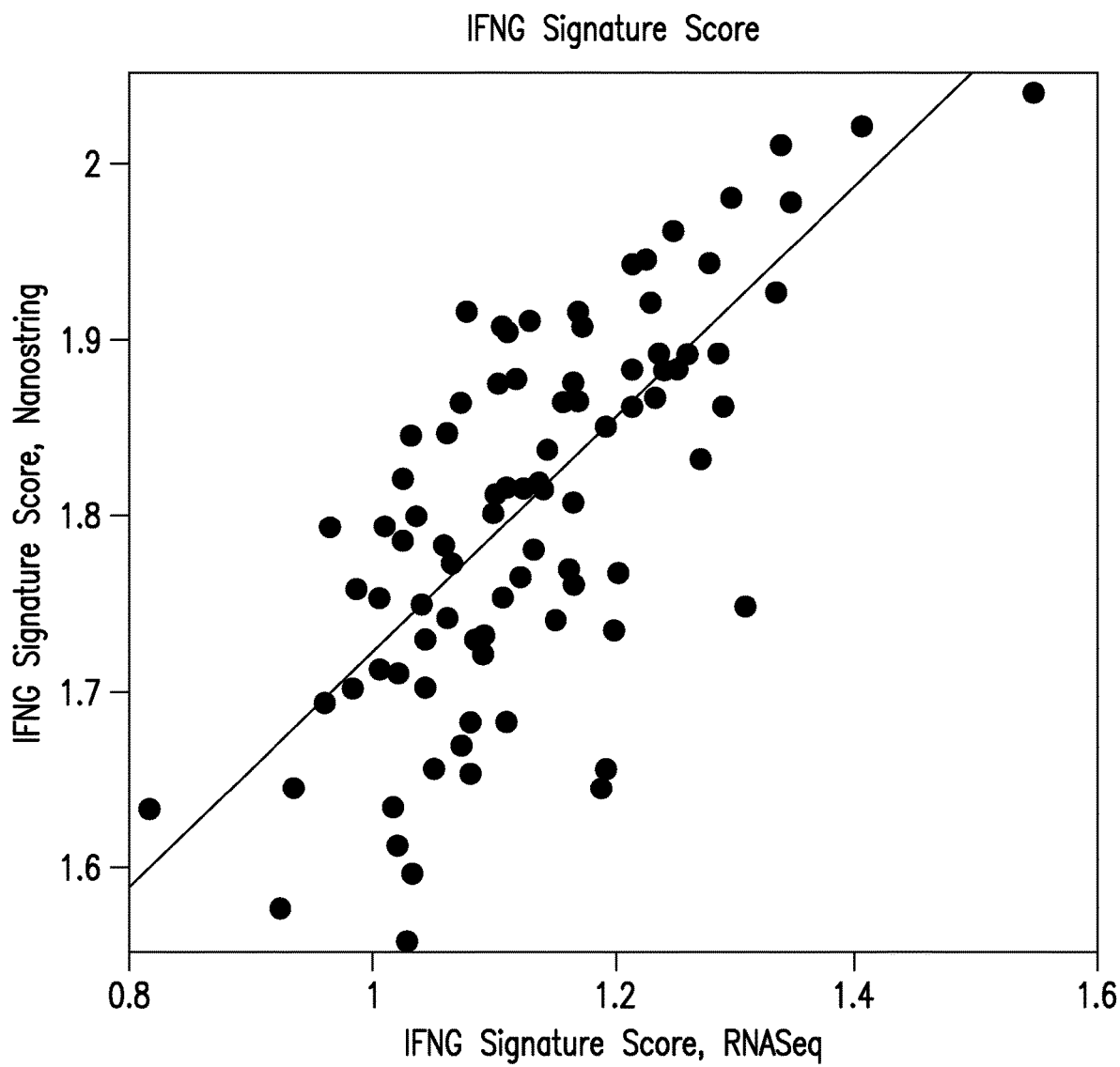
Figure 9:
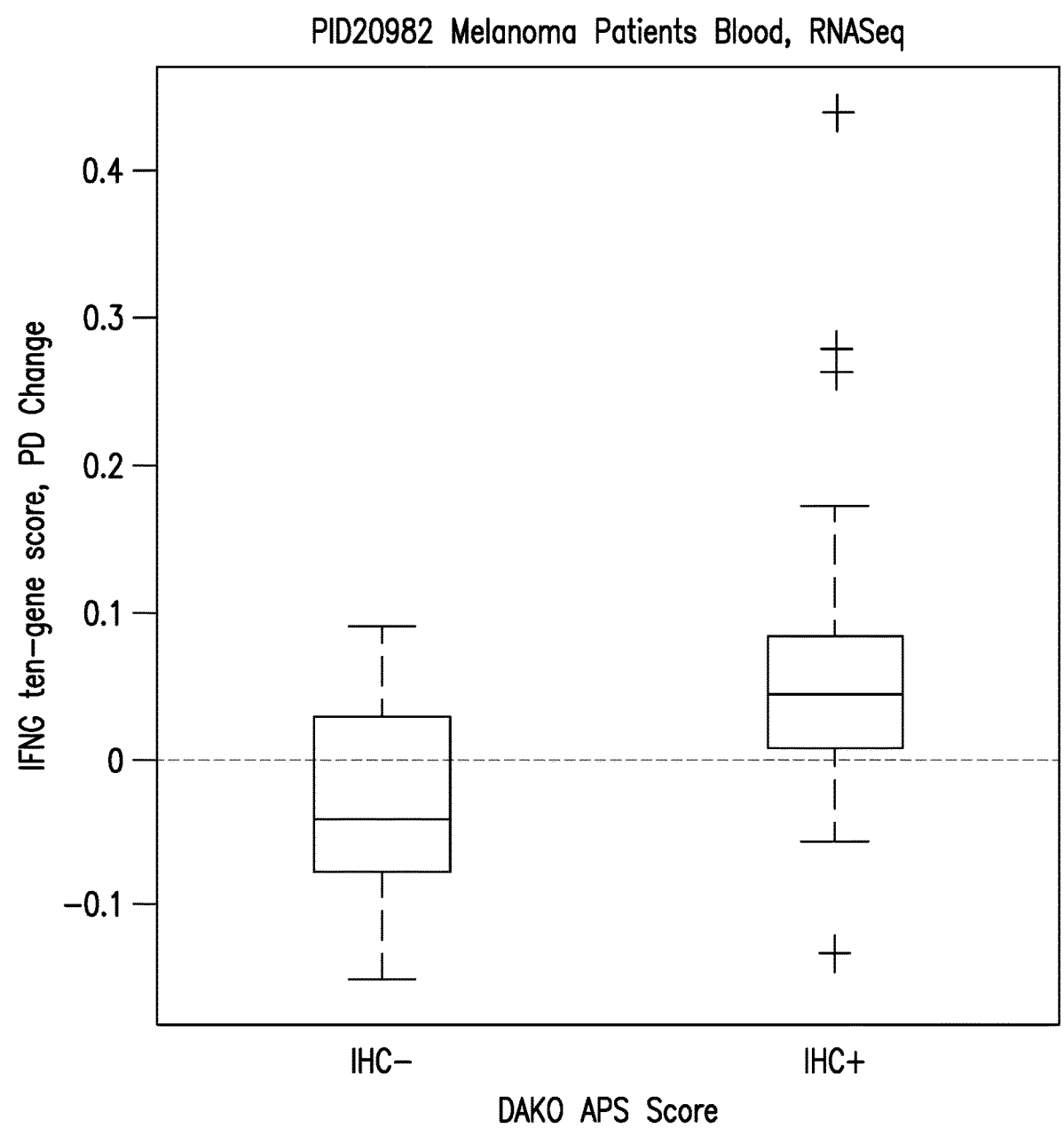
FIG. 9 is a box plot showing post-single dose (PD) changes in the scores in the MEL Cohort for an exemplary IFNG gene signature for subsets of the cohort that tested negative (IHC−) or positive (IHC+) for baseline PD-L1 tumor expression by immunohistochemical analysis using a prototype clinical assay developed by Dako.

These two signatures share several genes in common. To assess the relationship between these two signatures, a Fisher Exact test was performed, and the results are shown in FIG. 6. As shown in FIG. 6, 23 patients had positive post-dose changes in IFNG and PD-L1 signature scores, 9 patients had a negative post-dose score change for each of the IFNG and PD-L1 signatures, 8 patients had a negative post-dose change in the PD-L1 signature score and a positive change in the IFNG signature score, and 4 patients had a positive post-dose change in the PD-L1 signature score and a negative change in the IFNG signature score.

Other clinical endpoints were evaluated in the 44 Melanoma patient cohort. There was no clear association between post-dose changes in either of the IFNG and PD-L1 signatures with previous ipilimumab treatment received or the different pembrolizumab dosing schedules. In contrast to what had been observed in baseline tumor samples, baseline IFNG and PD-L1 signature scores in blood samples were not significantly associated with objective response or improved PFS. There appeared to be a possible association between the post-dose changes for the IFNG gene signature, as measured in the blood, with increased PD-L1 expression measured at baseline in the tumor.

Figure 10:
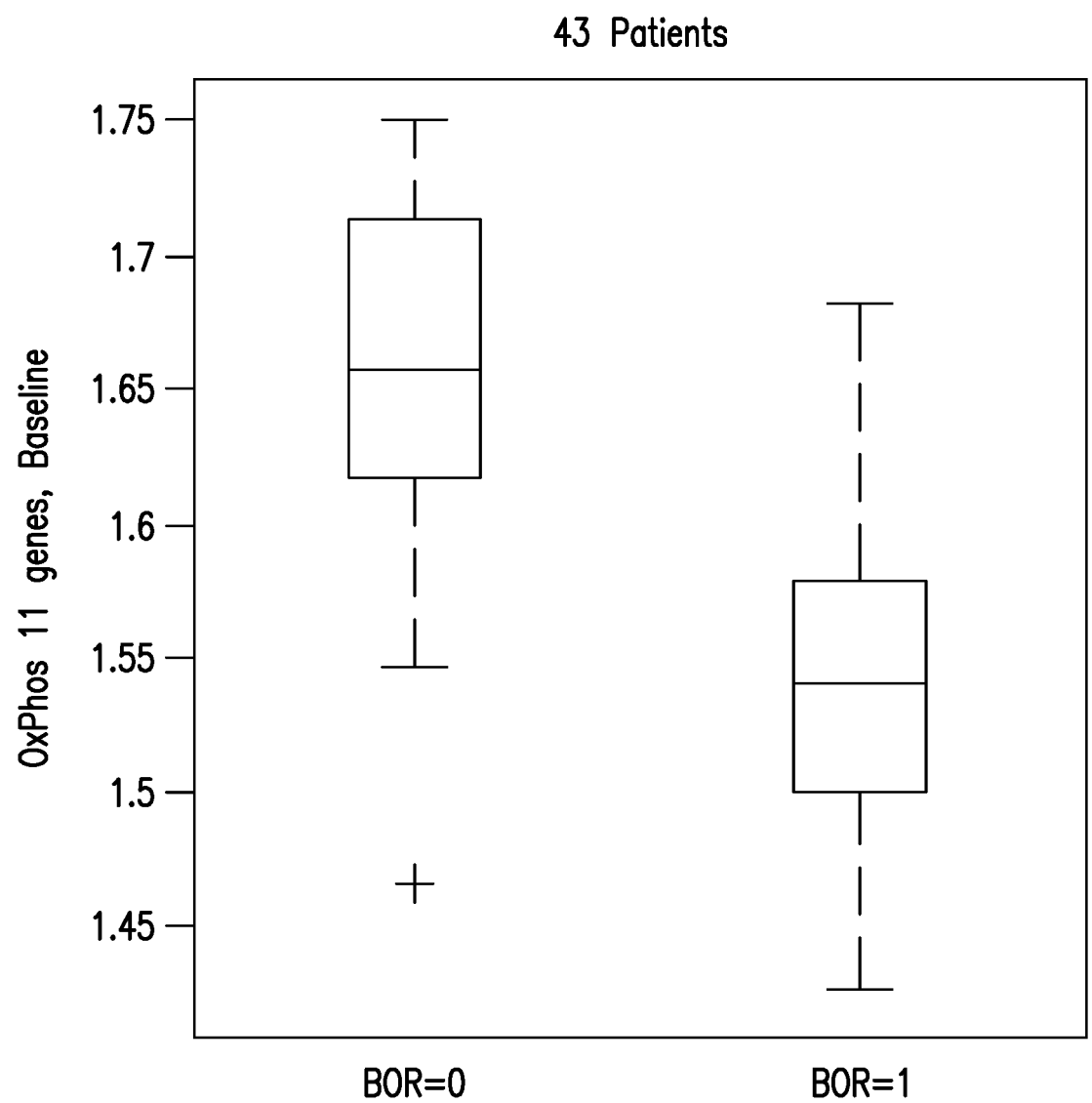
FIG. 10 is a box plot showing the distribution of scores for an exemplary OxPhos gene signature in 43 patients from the MEL cohort whose best objective response to pembrolizumab therapy was PR or CR (BOR=1) or did not have a PR or CR (BOR=0).
Figure 11:
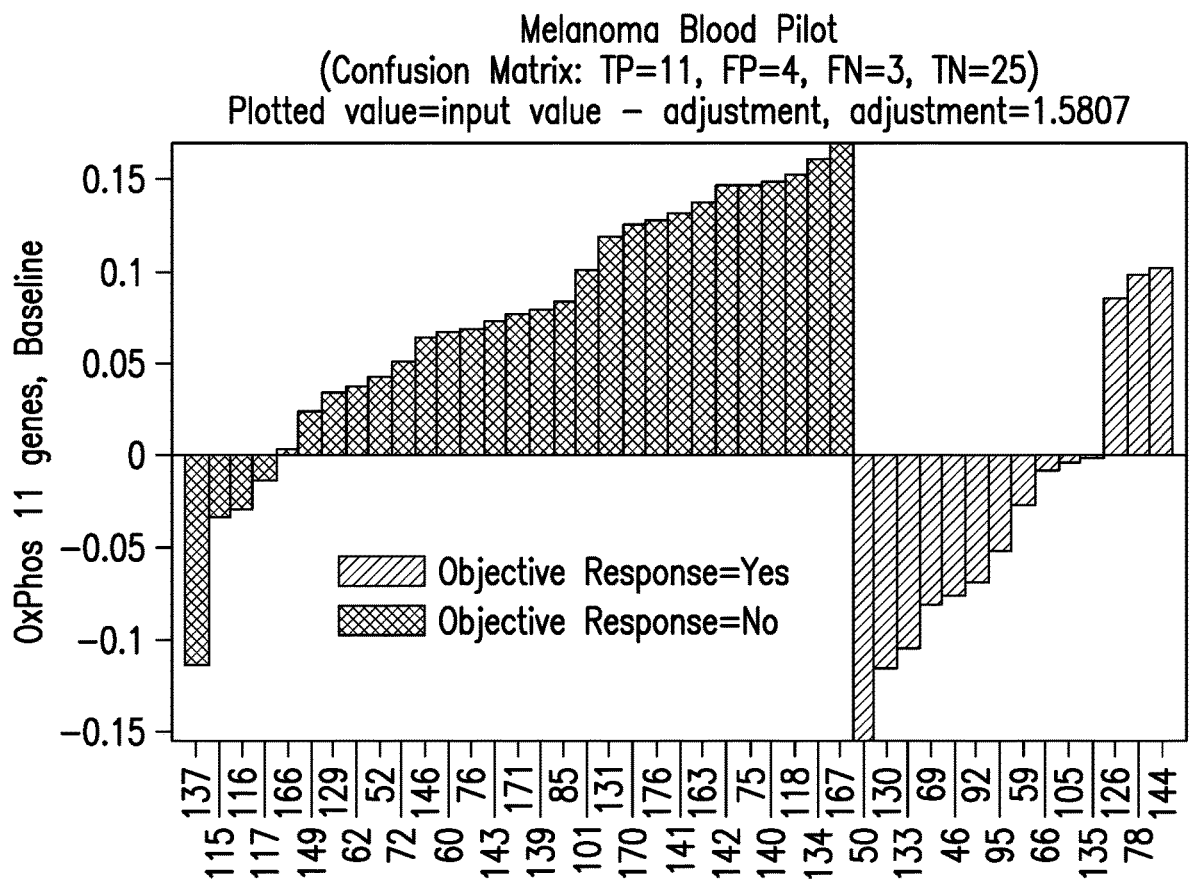
FIG. 11 is a waterfall plot of individual signature scores for an exemplary OxPhos gene baseline signature (Y axis) in 43 patients from the MEL Cohort (X-axis) who had an objective response (PR or CR) or did not have an objective response to pembrolizumab therapy.

After the inventors were un-blinded to clinical outcome data, post-hoc analyses were conducted to gain new insights into the biology associated with resistance or lack of response to pembrolizumab. Top ranked (nominal p-value <0.05) genes that were identified to be associated with resistance or poor response were input into ingenuity (IPA) pathway analysis for understanding possible biological connections. Pathway analysis identified metabolic dysregulation (Oxidative Phosphorylation) as one of the top pathways associated with poor response to pembrolizumab (see FIGS. 10-11).

The inventors also examined the predictive ability of a 6-gene IFNG signature (CXCL9, CXCL10, HLA-DRA, IDOL IFNG and STAT1) to predict anti-tumor response in blood samples from a cohort of ten Hodgkin's Lymphoma patients. Scores were calculated as the average of the normalized expression levels of each of the 6 signature genes. A Signed Rank Test was applied to pre- and post-dose patient blood samples to test for significance and was adjusted for multiplicity. The IFNG-induced gene set evaluated was significantly upregulated post a single dose of pembrolizumab with a P-value of 0.0020 (0.0039 adj.).

REFERENCES

1. Sharpe, A. H, Wherry, E. J., Ahmed R., and Freeman G. J. The function of programmed cell death 1 and its ligands in regulating autoimmunity and infection. *Nature Immunology* (2007); 8:239-245.
2. Dong H et al. Tumor-associated B7-H1 promotes T-cell apoptosis: a potential mechanism of immune evasion. Nat Med. 2002 August; 8(8):793-800.
3. Yang et al. PD-1 interaction contributes to the functional suppression of T-cell responses to human uveal melanoma cells in vitro. *Invest Ophthalmol Vis Sci*. 2008 June; 49(6 (2008): 49: 2518-2525.
4. Ghebeh et al. The B7-H1 (PD-L1) T lymphocyte-inhibitory molecule is expressed in breast cancer patients with infiltrating ductal carcinoma: correlation with important high-risk prognostic factors. *Neoplasia* (2006) 8: 190-198.
5. Hamanishi J et al. Programmed cell death 1 ligand 1 and tumor-infiltrating CD8+T lymphocytes are prognostic factors of human ovarian cancer. *Proceeding of the National Academy of Sciences* (2007): 104: 3360-3365.
6. Thompson R H et al. Significance of B7-H1 overexpression in kidney cancer. Clinical genitourin *Cancer* (2006): 5: 206-211.
7. Nomi, T. Sho, M., Akahori, T., et al. Clinical significance and therapeutic potential of the programmed death-1 ligand/programmed death-1 pathway in human pancreatic cancer. *Clinical Cancer Research* (2007); 13:2151-2157.
8. Ohigashi Y et al. Clinical significance of programmed death-1 ligand-1 and programmed death-1 ligand 2 expression in human esophageal cancer. *Clin. Cancer Research* (2005): 11: 2947-2953.
9. Inman et al. PD-L1 (B7-H1) expression by urothelial carcinoma of the bladder and BCG-induced granulomata: associations with localized stage progression. *Cancer* (2007): 109: 1499-1505.
10. Shimauchi T et al. Augmented expression of programmed death-1 in both neoplasmatic and nonneoplastic CD4+ T-cells in adult T-cell Leukemia/Lymphoma. *Int. J. Cancer* (2007): 121:2585-2590.
11. Gao et al. Overexpression of PD-L1 significantly associates with tumor aggressiveness and postoperative recurrence in human hepatocellular carcinoma. *Clinical Cancer Research* (2009) 15: 971-979.
12. Nakanishi J. Overexpression of B7-H1 (PD-L1) significantly associates with tumor grade and postoperative prognosis in human urothelial cancers. *Cancer Immunol Immunother*. (2007) 56: 1173-1182.
13. Hino et al. Tumor cell expression of programmed cell death-1 is a prognostic factor for malignant melanoma. *Cancer* (2010): 00: 1-9.
14. Ghebeh H. Foxp3+ tregs and B7-H1+/PD-1+T lymphocytes co-infiltrate the tumor *tissues of high-risk breast cancer patients: implication for immunotherapy. BMC Cancer.* 2008 Feb. 23; 8:57.
15. Ahmadzadeh M et al. Tumor antigen-specific CD8 T cells infiltrating the tumor express high levels of PD-1 and are functionally impaired. *Blood* (2009) 114: 1537-1544.
16. Thompson R H et al. PD-1 is expressed by tumor infiltrating cells and is associated with poor outcome for patients with renal carcinoma. *Clinical Cancer Research* (2007) 15: 1757-1761.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants to relate to each and every individual publication, database entry (e.g. Genbank sequences or GeneID entries), patent application, or patent, each of which is clearly identified, even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The invention claimed is:

1. A method of treating a patient diagnosed with a tumor which comprises:
   (a) collecting a baseline blood sample from the patient prior to administering a dose of a PD-1 antagonist to the patient,
   (b) administering at least one dose of a PD-1 antagonist to the patient for a treatment cycle,
   (c) collecting a post-dose blood sample from the patient after the treatment cycle of the at least one dose of the PD-1 antagonist,
   (d) obtaining a signature score for a gene signature biomarker in each of the baseline and post-dose blood samples, and (e) treating the patient with a therapeutic regimen that comprises administering a PD-1 antagonist if the post-dose signature score is greater than the baseline signature score or treating the subject with a therapeutic regimen that does not include administering a PD-1 antagonist if the post-dose score is equal to or less than the baseline score;
wherein the gene signature biomarker comprises PD-L1, PD-L2, LAG3, STAT1, and CXCL10.

2. The method of claim 1, wherein the gene signature biomarker comprises PD-L1, PD-L2, LAG3, STAT1, CXCL10, and CLEC10a.

3. The method of claim 2, wherein the gene signature biomarker comprises CCR5, CLEC10a, CXCL9, CXCL10, CXCL11, GZMA, HLA-DRA, IDO1, IFNG, LAG3, PD-L1, PD-L2, PRF1, and STAT1.

4. The method of claim 3, wherein the PD-1 antagonist is pembrolizumab in steps (b) and (e).

5. The method of claim 4, wherein the pembrolizumab is administered to the patient on day 1 of the treatment cycle, and the post-dose blood sample is collected on the last day of the treatment cycle or on the first day of a second treatment cycle, prior to administration of a first dose of the second treatment cycle.

6. The method of claim 3, wherein the PD-1 antagonist is administered to the patient on day 1 of the treatment cycle, and the post-dose blood sample is collected on the last day of the treatment cycle or on the first day of a second treatment cycle, prior to administration of a first dose of the second treatment cycle.

7. The method of claim 3, wherein the tumor is melanoma.

8. The method of claim 2, wherein the PD-1 antagonist is pembrolizumab in steps (b) and (e).

9. The method of claim 8, wherein the pembrolizumab is administered to the patient on day 1 of the treatment cycle, and the post-dose blood sample is collected on the last day of the treatment cycle or on the first day of a second treatment cycle, prior to administration of a first dose of the second treatment cycle.

10. The method of claim 2, wherein the PD-1 antagonist is administered to the patient on day 1 of the treatment cycle, and the post-dose blood sample is collected on the last day of the treatment cycle or on the first day of a second treatment cycle, prior to administration of a first dose of the second treatment cycle.

11. The method of claim 2, wherein the tumor is melanoma.

12. The method of claim 1, wherein the PD-1 antagonist is pembrolizumab in steps (b) and (e).

13. The method of claim 12, wherein the pembrolizumab is administered to the patient on day 1 of the first treatment cycle, and the post-dose blood sample is collected on the last day of the treatment cycle or on the first day of a second treatment cycle, prior to administration of a first dose of the second treatment cycle.

14. The method of claim 13, wherein the tumor is melanoma.

15. The method of claim 12, wherein the tumor is melanoma.

16. The method of claim 1, wherein the PD-1 antagonist is administered to the patient on day 1 of the treatment cycle, and the post-dose blood sample is collected on the last day of the treatment cycle or on the first day of a second treatment cycle, prior to administration of a first dose of the second treatment cycle.

17. The method of claim 12, wherein the tumor is melanoma.

18. The method of claim 1, wherein the tumor is melanoma.

* * * * *